(12) United States Patent
Antony

(10) Patent No.: US 12,053,438 B2
(45) Date of Patent: Aug. 6, 2024

(54) FORMULATION OF CURCUMINOIDS WITH ENHANCED BIOAVAILABILITY OF CURCUMIN, DEMETHOXYCURCUMIN, BISDEMETHOXYCURCUMIN AND METHOD OF PREPARATION AND USES THEREOF

(71) Applicant: ARJUNA NATURAL PRIVATE LIMITED, Alwaye (IN)

(72) Inventor: Benny Antony, Ankamaly (IN)

(73) Assignee: ARJUNA NATURAL PRIVATE LIMITED, Alwaye (IN)

( * ) Notice: Subject to any disclaimer, the term of this patent is extended or adjusted under 35 U.S.C. 154(b) by 1011 days.

(21) Appl. No.: 17/002,568

(22) Filed: Aug. 25, 2020

(65) Prior Publication Data
US 2020/0390727 A1 Dec. 17, 2020

Related U.S. Application Data

(60) Continuation-in-part of application No. 15/844,459, filed on Dec. 15, 2017, now Pat. No. 10,512,616, and a continuation-in-part of application No. 15/689,442, filed on Aug. 29, 2017, now Pat. No. 10,485,843, and a continuation-in-part of application No. 15/478,013, filed on Apr. 3, 2017, now abandoned, and a continuation of application No. 15/288,882, filed on Oct. 7, 2016, now abandoned, and a continuation-in-part of application No. 14/800,950, filed on Jul. 16, 2015, now Pat. No. 10,286,027, and a continuation-in-part of application No. 14/698,944, filed on Apr. 29, 2015, now Pat. No. 10,543,277, which is a continuation-in-part of application No. 14/623,608, filed on Feb. 17, 2015, now Pat. No. 9,878,040, which is a continuation-in-part of application No. 14/520,292, filed on Oct. 21, 2014, now Pat. No. 9,861,677, which is a continuation of application No. 14/476,555, filed on Sep. 3, 2014, now Pat. No. 10,159,654, which is a division of application No. 14/206,044, filed on Mar. 12, 2014, now Pat. No. 9,492,402, which is a continuation of application No. PCT/IN2014/000031, filed on Jan. 16, 2014, which is a division of application No. 14/094,725, filed on Dec. 2, 2013, now Pat. No. 8,895,087, which is a continuation of application No. PCT/IN2013/000673, filed on Oct. 31, 2013, which is a division of application No. 13/674,249, filed on Nov. 12, 2012, now Pat. No. 8,993,013, which is a division of application No. 13/645,031, filed on Oct. 4, 2012, now Pat. No. 8,859,020, which is a division of application No. 13/506,572, filed on Apr. 30, 2012, now Pat. No. 8,329,233, which is a division of (Continued)

(30) Foreign Application Priority Data

Apr. 5, 2010 (IN) .............................. 950CHE2010
Nov. 3, 2012 (IN) .............................. 4128CHE2012
Jan. 17, 2013 (IN) .............................. 226CHE2013

(51) Int. Cl.
*A61K 31/12* (2006.01)
*A61K 36/9066* (2006.01)

(52) U.S. Cl.
CPC .......... *A61K 31/12* (2013.01); *A61K 36/9066* (2013.01)

(58) Field of Classification Search
CPC ............ A61K 36/9066; A61K 2300/00; A61K 47/44; A61K 9/0053; A61K 47/46
See application file for complete search history.

(56) References Cited

U.S. PATENT DOCUMENTS 3,340,250 A 9/1967 Sair
5,120,538 A 6/1992 Oei
(Continued)

FOREIGN PATENT DOCUMENTS

CN 1483405 A 3/2004
CN 1489994 A 4/2004
(Continued)

OTHER PUBLICATIONS

Aratanechemuge, Y, Komiya, T, Moteki, H, Katsuzaki, H, Imai, K, and Hibasami, H, Selective Induction of Apoptosis by ar-Turmerone Isolated From Turmeric (*Curcuma longa* L) in Two Human Leukemia Cell Lines, But Not in Human Stomach Cancer Cell Line, International Journal of Molecular Medicine, 9:481-484 (2002).
Jayaprakasha, GK, Jena, BS, Negi, PS, and Sakariah, KK, Evaluation of Antioxidant Activities and Antimutagenicity of Turmeric Oil: A Byproduct from Curcumin Production, Biosciences, 57(9/10):828-835 (2002).
Kelloff, GJ, Crowell, JA, Hawk ET, Steele, VE, Lubet, RA, Boone, CW, Covey JM, Doody, LA, Omenn, GS, Greenwald, P, Hong, WK, Parkinson, DR, Bagheri, D, Baxter, GT, Blunden, M, Doeltz, MK, Eisenhauer, KM, Johnson, K, Knapp, GG, Longfellow, DG, Malone, WF, Nayfield, SG, Seifried, HE, Swall, LM, and Sigman, CC, Strategy and Planning for Chemopreventive Drug Development: Clinical Development Plans II, Journal of Cellular Biochemistry, 26S: 54-71 (1996).

(Continued)

*Primary Examiner* — Aaron J Kosar
(74) *Attorney, Agent, or Firm* — Jyoti C. Iyer

(57) ABSTRACT

A formulation of curcuminoid mixture having curcumin, demethoxycurcumin and bisdemethoxycurcumin and an essential oil of turmeric having 45% Ar-turmerone. The formulation gives enhanced bioavailability of bisdemethoxycurcumin, demethoxycurcumin and curcumin for up to 10 hrs. The curcuminoid mixture has curcumin, demethoxycurcumin and bisdemethoxycurcumin in a weight/weight ratio ranging from about 0.8:1:1 to about 1:1.1:1.2. A process of preparing a formulation of curcuminoid mixture having curcumin, demethoxycurcumin and bisdemethoxycurcumin in 0.8:1:1 to 1:1.1:1.2 weight/weight ratio and an essential oil of turmeric having 45% Ar-turmerone. A formulation for improved biological activity and bioavailability and tissue distribution of curcumin, demethoxycurcumin and bisdemethoxycurcumin.

8 Claims, 2 Drawing Sheets

Related U.S. Application Data application No. 13/385,717, filed on Mar. 5, 2012, now Pat. No. 8,623,431, which is a continuation-in-part of application No. PCT/IN2011/000232, filed on Apr. 4, 2011, which is a division of application No. 12/926,980, filed on Dec. 21, 2010, now Pat. No. 8,197,869, which is a division of application No. 12/926,985, filed on Dec. 21, 2010, now Pat. No. 8,153,172, which is a division of application No. 12/662,740, filed on Apr. 30, 2010, now Pat. No. 7,879,373, which is a division of application No. 12/073,864, filed on Mar. 11, 2008, now Pat. No. 7,883,728, which is a division of application No. 11/635,599, filed on Dec. 8, 2006, now Pat. No. 7,736,679, which is a continuation of application No. PCT/IN2005/000176, filed on May 30, 2005.

(60) Provisional application No. 61/794,175, filed on Mar. 15, 2013.

(56) References Cited

U.S. PATENT DOCUMENTS

| | | | |
|---|---|---|---|
| 5,536,506 | A | 7/1996 | Majeed et al. |
| 5,861,415 | A | 1/1999 | Majeed et al. |
| 6,224,871 | B1 | 5/2001 | Hastings et al. |
| 6,224,877 | B1 | 5/2001 | Gaikar et al. |
| 6,235,287 | B1 | 5/2001 | Weidner et al. |
| 6,245,350 | B1 | 6/2001 | Amey et al. |
| 6,344,475 | B1 | 2/2002 | Caplan et al. |
| 6,576,273 | B2 | 6/2003 | Madsen et al. |
| 6,592,896 | B2 | 7/2003 | Rosenbloom |
| 6,827,951 | B2 | 12/2004 | Newmark et al. |
| 6,942,881 | B2 | 9/2005 | Madsen et al. |
| 6,982,099 | B2 | 1/2006 | Newmark et al. |
| 6,991,814 | B2 | 1/2006 | Ray et al. |
| 7,037,524 | B2 | 5/2006 | Gow et al. |
| 7,041,321 | B2 | 5/2006 | Newmark et al. |
| 7,067,159 | B2 | 6/2006 | Newmark et al. |
| 7,070,816 | B2 | 7/2006 | Newmark et al. |
| 7,736,679 | B2 * | 6/2010 | Antony ............... A61P 39/06 424/725 |
| 7,879,373 | B2 * | 2/2011 | Antony ............... A61P 25/28 424/773 |
| 7,883,728 | B2 * | 2/2011 | Antony ............... A61P 1/18 424/773 |
| 8,153,172 | B2 * | 4/2012 | Antony ............... A61P 43/00 424/773 |
| 8,197,869 | B2 * | 6/2012 | Antony ............... A61P 9/00 424/773 |
| 8,329,233 | B2 * | 12/2012 | Antony ............... A61P 9/00 424/443 |
| 8,623,431 | B2 * | 1/2014 | Antony ............... A61P 25/00 424/756 |
| 8,859,020 | B1 * | 10/2014 | Antony ............... A61K 31/12 424/773 |
| 8,895,087 | B2 * | 11/2014 | Antony ............... A61P 29/00 424/725 |
| 8,993,013 | B2 * | 3/2015 | Antony ............... A61P 35/02 424/773 |
| 9,492,402 | B2 * | 11/2016 | Antony ............... A61K 31/12 |
| 9,861,677 | B2 * | 1/2018 | Antony ............... A61P 29/00 |
| 9,878,040 | B2 * | 1/2018 | Antony ............... A61P 1/16 |
| 10,286,027 | B2 * | 5/2019 | Antony ............... A61K 31/12 |
| 2002/0136786 | A1 | 9/2002 | Newmark et al. |
| 2004/0247664 | A1 | 12/2004 | Dreja et al. |
| 2005/0123632 | A1 | 6/2005 | Chen et al. |
| 2006/0051438 | A1 | 3/2006 | Ray et al. |

FOREIGN PATENT DOCUMENTS

| | | |
|---|---|---|
| CN | 1491089 A | 4/2004 |
| CN | 1548121 A | 11/2004 |
| EP | 1465646 A1 | 10/2004 |
| IN | 457/RQ/CHE/2003 | 7/2005 |
| IN | 200430 | 5/2006 |
| JP | 2000-228966 A | 8/2000 |
| JP | 2004524304 A | 8/2004 |
| JP | 2004331539 A | 11/2004 |
| WO | WO 2000/059523 A1 | 10/2000 |
| WO | WO 2001/000201 A1 | 1/2001 |
| WO | WO 2002/032444 A1 | 4/2002 |
| WO | WO 02074295 A1 | 9/2002 |
| WO | WO 03/049753 A1 | 6/2003 |
| WO | WO 03/075685 A1 | 9/2003 |

OTHER PUBLICATIONS

Rao, CV, Rivenson, A, Simi, B, and Reddy, BS, Chemoprevention of Colon Carcinogenesis by Dietary Curcumin, a Naturally Occuring Plant Phenolic Compound, Cancer Research, 55:259-266 (1995).

Subramanian, M, Sreejayan, Rao, MNA, Devasagayam, TPA, and Singh, BB, Diminution of Singlet Oxygen-Induced DNA Damage by Curcumin and Related Antioxidants, Mutation Research, 311:249-255 (1994).

Tennesen, HH, and Greenhill, JV, Studies on Curcumin and Curcuminoids, XXII: Curcumin as a Reducing Agent and as a Radical Scavenger, International Journal of Pharmaceutics, 87:79-87 (1992).

Reddy, ACP, and Lokesh, BR, Studies on the Inhibitory Effects of Curcumin and Eugenol on the Formation of Reactive Oxygen Species and the Oxidation of Ferrous Iron, Molecular and Cellular Biochemistry, 137:1-8 (1994).

Donatus, IA, Sardjoko, and Vermeulen, NPE, Cytotoxic and Cytoprotective Activities of Curcumin, Biochemical Pharmacology, 39(12):1869-1875 (1990).

Sharma, SC, Mukhtar, H, Sharma, SK, Murti, CRK, Lipid Peroxide Formation in Experimental Inflammation, Biochemical Pharmacology, 21:1210-1214 (1972).

Liu, J-Y, Lin, S-J, and Lin, J-K, Inhibitory Effects of Curcumin on Protein Kinase C Activity Induced by 12-O-tetradecanoyl-Phorbol-13-Acetate in NIH 3T3 Cells, Carcinogenesis, 14(5):857-861 (1993).

Huang, T-S, Lee, S-C, and Lin, J-K, Suppression of c-Jun/ AP-1 Activation by an inhibitor of Tumor Promotion in Mouse Fibroblast Cells, Proc. Natl. Acad. Sci. U.S.A., 88:5292-5296 (1991).

Huang, M-T, Lysz, T, Ferraro, T, and Conney, AH, Inhibitory Effects of Curcumin on Tumor Promotion and Arachidonic Acid Metabolism in Mouse Epidermis, Cancer Chemoprevention, pp. 375-391 (1992), CRC Press, Inc.

Huang, M-T, Lysz, T, Ferraro, T, Abidi, TF, Laskin, JD, and Conney, AH, Inhibitory Effects of Curcumin on In Vitro Lipoxygenase and Cyclooxygenase Activities in Mouse Epidermis, Cancer Research, 51:813-819 (1991).

Plummer, SM, Holloway, KA, Manson, MM, Munks, RJL, Kaptein, A, Farrow, S, and Howells, L, Inhibition of Cyclo-Oxygenase 2 Expression in Colon Cells by the Chemopreventive Agent Curcumin Involves Inhibition of NF-KB Activation via the NIK/IKK Signalling Complex, Oncogene, 18:6013-6020 (1999).

Funk, CD, Funk, LB, Kennedy, ME, Pong, AS, and Fitzgerald, GA, Human Platelet / Erythroleukemia Cell Prostaglandin G/H Synthase: cDNA Cloning, Expression, and Gene Chromosomal Assignment, FASEB Journal, 5:2304-2312 (1991).

Subbaramaiah, K, Telang, N, Ramonetti, JT, Araki, R, Devito, B, Weksler, BB, and Dannenberg, AJ, Transcription of Cyclooxygenase-2 Is Enhanced in Transformed Mammary Epithelial Cells, Cancer Research, 56:4424-4429 (1996).

Dubois, RN, Awad, J, Morrow, J, Roberts, LJ, and Bishop, PR, Regulation of Eicosanoid Production and Mitogenesis in Rat Intestinal Epithelial Cells by Transforming Growth Factor-α and Phorbol Ester, J. Clin. Invest., 93:493-498 (1994).

Kelley, DJ, Mestre, JR, Subbaramaiah, K, Sacks, PG, Schantz, SP, Tanabe, T, Inoue, H, Ramonetti, JT, and Dannenberg, AJ, Benzo[a]pyrene Up-Regulates Cyclooxygenase-2 Gene Expression in Oral Epithelial Cells, Carcinogenesis, 18(4):795-799 (1997).

Huang, M-T, Smart, RC, Wong, C-Q, and Conney, AH, Inhibitory Effect of Curcumin, Chlorogenic Acid, Caffeic Acid, and Ferulic

(56) References Cited

OTHER PUBLICATIONS

Acid on Tumor Promotion in Mouse Skin by 12-O-Tetradecanoylphorbol-13-Acetate, Cancer Research, 48:5941-5946 (1988).
Asai, A and Miyazawa, T, Occurence of Orally Administered Curcuminoid as Glucuronide and Glucuronide/Sulfate Conjugates in Rat Plasma, Life Sciences, 67:2785-2793 (2000).
Ravindranath, V, and Chandrasekhara, N, In Vitro Studies on the Intestinal Absorption of Curcumin in Rats, Toxicology, 20:251-257 (1981).
Limtrakul, P, Lipigorngoson, S, Namwong, O, Apisariyakul, A, and Dunn, FW, Inhibitory Effect of Dietary Curcumin on Skin Carcinogenesis in Mice, Cancer Letters, 116:197-203 (1997).
Inano, H, and Onoda, M, Prevention of Radiation-Induced Mammary Tumors, Int. J. Radiation Oncology Biol. Phys., 52(1):212-223 (2002).
Inano, H, and Onoda, M, Radioprotective Action of Curcumin Extracted From Curcuma Longa Linn: Inhibitory Effect on Formation of Urinary 8-Hydroxy-2-Deoxyguanosine, Tumorigenesis, But Not Mortality, Induced by $\gamma$-Ray Irradiation, Int. J. Radiation Oncology Biol. Phys., 53(3):735-743 (2002).
Shoba, G, Joy, D, Joseph, T, Majeed, M, Rajendran, R, and Srinivas, PSSR, Influence of Piperine on the Pharmacokinetics of Curcumin in Animals and Human Volunteers, Planta Medica, 64:353-356 (1998).
Began, G, Sudharshan, E, Sankar, KU, and Rao, AGA, Interaction of Curcumin With Phosphatidylcholine: A Spectrofluorometric Study, J. Agric. Food Chem, 47:4992-4997 (1999).
Lantz, RC, Chen, GJ, Solyom, AM, Jolad, SD, and Timmermann, BN, The Effect of Turmeric Extracts on Inflammatory Mediator Production, Phytomedicine 12:445-452 (2005).
Nishiyama, T, Mae, T, Kishida, H, Tsukagawa, M, Mimaki, Y, Kuroda, M, Sashida, Y, Takahashi, K, Kawada, T, Nakagawa, K, and Kitahara, M, Curcuminoids and Sesquiterpenoids in Turmeric (*Curcuma longa* L) Suppress an Increase in Blood Glucose Level in Type 2 Diabetic KK-A$^y$ mice, J. Agric. Food Chem, 53:959-963 (2005).
Li, L, Braiteh, FS, and Kurzrock, R, Liposome-Encapsulated Curcumin, In Vitro and In Vivo Effects on Proliferation, Apoptosis, Signaling, and Angiogenesis, Cancer, 104(6):1322-1331 (2005).
Kumar, V, Lewis, SA, Mutalik, S, Shenoy, DB, Venkatesh and Udupa, N, Biodegradable Microspheres of Curcumin for Treatment of Inflammation, Indian J Physical Pharmacol, 46(2): 209-217 (2002).
Ammon, HPT, and Wahl, MA, Pharmacology of Curcuma Longa, Planta Med, 57:1-7, (1991).
Ravindranath, V, and Chandrasekhara, N, Absorption and Tissue Distribution of Curcumin in Rats, Toxicology, 16: 259-265 (1980).
Wahlstrom, B and Blennow, G, A Study on the Fate of Curcumin in the Rat, Acta Pharmacol. et Toxicol., 43:86-92 (1978).
Monograph, *Curcuma longa* (Turmeric), Alternative Medicine Review, vol. 6 (Supplement): S62-S66 (2001).
Piyachaturawat, P, Glinsukon, T, and Toskulkao, C, Acute and Subacute Toxicity of Piperine in Mice, Rats and Hamsters, Toxicology Letters, 16:351-359 (1983).
Matsuo, T, Toyota, A, Kanamori, H, Nakamura, K, Katsuki, S, Sekita, S, and Satake, M, Constituents of Representative Curcuma and Estimation of *Curcuma* Species in Health Foods, Bulletin of the Hiroshima Prefectural Institute of Public Health and Environment, 10:7-13 (2002), Japan Science and Technology Agency.
Kawamori, T, Lubet, R, Steele, VE, Kelloff, GJ, Kaskey, RB, Rao, CV, and Reddy, BS, Chemopreventive Effect of Curcumin, A Naturally Occuring Anti-Inflammatory Agent, During the Promotion/Progression Stages of Colon Cancer, Cancer Res., 59:597-601 (1999), American Association for Cancer Research.
Mahmoud, NN, Carothers, AM, Grunberger, D, Bilinski, RT, Churchill, MR, Martucci, C, Newmark, HL, and Bertagnolli, MM, Plant Phenolics Decrease Intestinal Tumors in an Animal Model of Familial Adenomatous Polyposis, Carcinogenesis, 21(5):921-927 (2000), Oxford University Press.

Zhang, F, Altorki, NK, Mestre, JR, Subbaramaiah, K, and Dannenberg, AJ, Curcumin Inhibits Cyclooxygenase-2 transcription in Bile Acid- and Phorbol Ester-Treated Human Gastrointestinal Epithelial Cells, Carcinogenesis, 20(3): 445-451 (1999), Oxford University Press.
Ireson, C, Orr, S, Jones, DJL, Verschoyle, R, Lim, C-K, Luo, J-L, Howells, L, Plummer, S, Jukes, R, Williams, M, Steward, WP, and Gescher, A, Characterization of Metabolites of the Chemopreventive Agent Curcumin in Human and Rat Hepatocytes and in the Rat in Vivo, and Evaluation of Their Ability to Inhibit Phorbol Ester-Induced Prostaglandin $E_2$ Production, Cancer Res., 61: 1058-1064 (2001), American Association for Cancer Research.
Sharma, RA, McLelland, HR, Hill, KA, Ireson CR, Euden, SA, Manson MM, Pirmohamed, M, Marnet, LJ, Gescher, AJ, and Steward, WP, Pharmacodynamic and Pharmacokinetic Study of Oral Curcuma Extract in Patients with Colorectal Cancer, Clin. Cancer Res., 7:1894-1900 (2001), American Association for Cancer Research.
Pan, M-H, Huang, T-M, and Lin, J-K, Biotransformation of Curcumin Through Reduction and Glucoronidation in Mice, Drug Metabolism and Disposition, 27(1):486-494 (1999), American Society for Pharmacology and Experimental Therapeutics.
Ireson, CR, Jones, DJL, Orr, S, Coughtrie, MWH, Boocock, DJ, Williams, ML, Farmer, PB, Steward, WP, and Gescher, AJ, Metabolism of the Cancer Chemopreventive Agent Curcumin in Human and Rat Intestine, Cancer Epidemiology, Biomarkers & Prevention, 11:105-111 (2002), American Association for Cancer Research.
Perkins, S, Verschoyle, RD, Hill, K, Parveen, I, Threadgill, MD, Sharma, RA, Williams, ML, Steward, WP, and Gescher, AJ, Chemopreventive Efficacy and Pharmacokinetics of Curcumin in the Min/+ Mouse, A Model of Familial Adenomatous Polyposis, Cancer Epidemiology, Biomarkers & Prevention, 11: 535-540 (2002), American Association for Cancer Research.
Chuang, SE, Kuo, ML, Hsu, CH, Chen, CR, Lin, JK, Lai, GM, Hsieh, CY, and Cheng, AL, Curcumin-Containing Diet Inhibits Diethylnitrosamine-Induced Murine Hepatocarcinogenesis, Carcinogenesis, 21(2):331-335 (2000), Oxford University Press.
Inano, H, Onoda, M, Inafuku, N, Kubota, M, Kamada, Y, Osawa, T, Kobayashi, H, and Wakabayashi, K, Potent Preventive Action of Curcumin on Radiation-Induced Initiation of Mammary Tumorigenesis in Rats, Carcinogenesis, 21(10): 1835-1841 (2000), Oxford University Press.
Garcea, G, Berry, DP, Jones, Djl, Singh, R, Dennison, AR, Farmer, PB, Sharma, RA, Steward, WP, and Gescher, AJ, Consumption of the Putative Chemopreventive Agent Curcumin by Cancer Patients: Assessment of Curcumin Levels in the Colorectum and their Pharmacodynamic Consequences, Cancer Epidemiology, Biomarkers & Prevention, 14(1) 120-125 (2005), American Association for Cancer Research.
Govindarajan, VS and Stahl, WH, Turmeric—Chemistry, technology, and Quality, CRC Critical Reviews in Food Science and Nutrition, 12(3):199-301 (1980).
Sharma RA, Ireson, CR, Verschoyle, RD, Hill, KA, Williams, ML, Leuratti, C, Manson, MM, Marnett, LJ, Steward, WP, and Gescher, A, Effects of Dietary Curcumin on Glutathione S-Transferase and Malondialdehyde-DNA Adducts in Rat Liver and Colon Mucosa: Relationship with Drug Levels, Clinical Cancer Research, 7:1452-1458 (2001).
Sharma, RA, Euden, SA, Platton, SL, Cooke, DN, Shafayat, A, Hewitt, HR, Marczylo, TH, Morgan, B, Hemigway, D, Plummer, SM, Pirmohamed, M, Gescher, AJ and Steward, WP, Phase I Clinical Trial of Oral Curcumin: Biomarkers of Systemic Activity and Compliance, Clinical Cancer Research, vol. 10, 6847-6854 (Oct. 15, 2004).
Hong CH, Kim Y, and Lee SK, Sesquiterpenoids from the Rhizome of Curcuma Zedoaria, Arch Pharm Res., 24(5): 424-426 (2001).
G. Scapagnini, R Foresti, V. Calabrese, AM Giuffrida Stella, CJ Green, and R. Motterlini, Caffeic Acid Phenethyl Ester and Curcumin: A Novel Class of Heme Oxygenase-1 Inducers, Molecular Pharmacology, 61(3):554-561 (2002).
Supplementary European Search Report (3 pages) dated Dec. 14, 2009.
Anna Carolina CM Manzan, Toniolo FS, Bredow E, and Povh, NP, Extraction of Essential Oil and Pigments from *Curcuma longa* [L.]

(56) References Cited

OTHER PUBLICATIONS by Steam Distillation and Extraction with Volatile Solvents, Journal of Agricultural and Food Chemistry, 51:6802 6807 (2003).
Negi PS, Jayaprakasha GK, Rao LJM, and Sarkaria KK, Antibacterial Activity of Turmeric Oil: A Byproduct from Curcumin Manufacture, J. Agric. Food Chem., 47:4297-4300 (1999).
Hong CH, Noh MS, Lee WY and Lee SK, Inhibitory Effects of Natural Sesquiterpenoids Isolated from the Rhizomes of Curcuma zedoaria on Prostaglandin E2 and Nitric Oxide Production, Planta Med, 68:545-547 (2002).
Craig WJ, The Golden Touch of Turmeric, Vibrant Life, 19 (3): 38-39 (2003), ProQuest Central.
Sandur SK, Pandey MK, Sung B, Ahn KS, Murakami A, Sethi G, Limtrakul P, Badmaev V and Aggarwal BB, Curcumin, Demethoxycurcumin, Bisdemethoxycurcumin, Tetrahydrocurcumin and Turmerones Differentially Regulate Anti-Inflammatory and Anti-Proliferative Responses Through a ROS-Independent Mechanism, Carcinogenesis Advance Access, originally published online on May 23, 2007, Carcinogenesis 28(8):1765-1773 (2007); doi:10.1093/carcin/bgm123.
Asche SL and Thakkar SK, Oil Extraction Increases Curcumin Availability from Turmeric Sources, FASEB Journal, 18 (4-5): Abstract 115.7 (2004).
Fujii Masami et al., Ingredient that improves bio-availability of curcumin, latest edition of Natural Food coloring material, Korin Publishing Co., Ltd., pp. 168-172 (2001).
Janaki, N and Bose, JL, An Improved Method For the Isolation of Curcumin From Turmeric, *Curcuma Longa*, L, Journal of Indian Chemical Society, 44 (11):985-986 (1967).
Krishnamurthy, N, Mathew, AG, Nambudiri, ES, Shivashankar, S, Lewis, YS, and Natarajan, CP, Oil and Oleoresin of Turmeric, Trop. Sci., 18(1):37-45 (1976).
Huang, M-T, Lou, Y-R, MA, W, Newmark, HL, Reuhl, KR and Conney, AH, Inhibitory Effects of Dietary Curcumin on Forestomach, Duodenal, and Colon Carcinogenesis in Mice, Cancer Research, 54:5841-5847 (1994).
Pabon, HJJ, A Synthesis of Curcumin and Related Compounds, Recueil, 83:379-386 (1964).
Xu, Y, Ku, B-S, Yao, H-Y, Lin, Y-H, Ma, X, Zhang, Y-H, Li, X-J, Antidepressant effects of curcumin in the forced swim test and olfactory bulbectomy models of depression in rats, Pharmacology Biochemistry and Behavior, 82(1): 200-206 (2005), Elsevier, Inc.
Yu, ZF, Kong, LD, and Chen, Y, Antidepressant activity of aqueous extracts of Curcuma longa in mice, Journal of Ethnopharmacology, 83(1-2): 161-165 (2002), Elsevier Science Ireland Ltd.
Funk, JL, Oyarzo, JN, Frye, JB, Chen, G, Lantz, RC, Jolad, SD, Solyom, Am, and Timmermann, BN, Turmeric extracts containing curcuminoids prevent experimental rheumatoid arthritis, Journal of Natural Products, 69(3): 351-355 (2006), American Chemical Society and American Society of Pharmacology.
Begum, AN, Jones, MR, Lim, GP, Morihara, T, Kim, P, Heath, DD, Rock, CL, Pruitt, MA, Yang, F, Hudspeth, B, Hu, S, Faull, KF, Teter, B, Cole, GM, and Frautschy, SA, Curcumin structure-function, bioavailability, and efficacy in models of neuroinflammation and Alzheimer's disease, Journal of Pharmacology and Experimental Therapeutics, 326(1): 196-208 (2008).
Zhang, L, Fiala, M, Cashman, J, Sayre, J, Espinosa, A, Mahanian, M, Zaghi, J, Graves, MC, Bernard, G and Rosenthal, M, Curcuminoids enhance amyloid-β uptake by macrophages of Alzheimer's disease patients, Journal of Alzheimer's Disease, 10(1):1-7 (2006), IOS Press and the authors.

Eight (8) pages of Supplementary European Search Report of Sep. 10, 2013 in Application No. EP 11765176.
Hashibe, M, Sankaranarayanan, R, Thomas, G, Kuruvilla, B, Mathew, B, Somanathan, T, Parkin,DM and Zhang, ZF, Alcohol drinking, body mass index and the risk of oral Leukoplakia in an Indian population, Int. J. Cancer, 88: 129-134 (2000).
Kaur, J, Srivastava, A, Ralhan, R, Over expression of p53 protein in betel and tobacco related human oral dysplasia and squamous cell carcinoma in India, Int. J. Cancer: Aug. 1; 58(3):3405.(1994).
Sol, S, Bilimoria, KF, Bhargava, K, Mani, NJ, Shah, RA, Cytologic, histologic and clinical correlations of precancerous and cancerous oral lesions in 57,518 industrial workers of Gujarat, India, Acta Cytol. Mar.-Apr. 1977;21(2):196-8.
Silverman, S, Bhargava, K, Smith, LW, Malaowalla, AM, Malignant transformation and natural history of oral leukoplakia in 57,518 industrial workers of Gujarat, India, Cancer.Oct; 38(4):1790-5 (1976).
Danely,P, Slaughterm, D, Harry, W , Southwickm, D, Walter Smejkal, MD, Field Cancerization in oral stratified Squamous epithelium, Sixth Annual Cancer Symposium of the James Ewing Society, Mar. 7 (1953).
Saleheen, D, Ali, SA, Ashfaq, K, Siddiqui, AA, Agha, A and Yasinzai, MM, Latent activity of curcumin against Leishmaniasis in Vitro, Biol. Pharm. Bull. 25(3): 386-389 (2002).
Koide, T, Nose, M, Ogihara, Y, Yoshisada Yabu, Y, and Ohta, N, Leishmanicidal effect of curcumin in Vitro, Biol. Pharm. Bull. 25(1): 131-133 (2002).
Gomes,DCE, Alegrio,LV, Lima,MEF, Leon,LL,Araujo,CAC, Synthetic derivatives of curcumin and their activity against Leishmania amazonensis, Arzneim-Forsch/Drug Res.52,No. 2: 120-124 (2002).
Wu, NC, Safety and Anti-Inflammatory Activity of Curcumin: A Component of Tumeric (*Curcuma longa*), The Journal of Alternative and Complementary Medicine vol. 9, No. 1, pp. 161-168 (2003).
Strong, MS, I.J., Vaughan, CW, Field cancerization in the aerodigestive tract—its etiology, manifestation, and significance, J Otolaryngol, 13(1): p. 1-6 (1984).
Pandey, M, Thomas, G, Somanathan, T, Sankaranarayanan, R, Abraham, E K., Jacob, B J, and Mathew, B, Evaluation of surgical excision of non-homogeneous oral leukoplakia in a screening intervention trial, Kerala, India. Oral Oncol,. 37: p. 103-9 (2001).
Grosso C, Valentao P, Ferreres F and Andrade PB, The use of flavonoids in central nervous system disorders, Current Medicinal Chemistry, 20:1-26 (2013).
Bergman J, Midownik C, Bersudsky Y, Sokolik S, Lerner PP, Krenin A, Polakiewicz J and Lerner V, Curcumin as an Add-On to Antidepressive Treatment: A Randomized, Double-Blind, Placebo-Controlled, Pilot Clinical Study, Clinical Neuropharm, 36:73-77 (2013).
Guidance for Industry Estimating the Maximum Safe Starting Dose in Initial Clinical Trials for Therapeutics in Adult Healthy Volunteers; U.S. Department of Health and Human Services Food and Drug Administration Center for Drug Evaluation and Research (CDER) (referred to as "Guidance") JA\!GUIDANC\5541fnlcln1.doc, pp. 1-27 (Jul. 6, 2005).
Antony, B, Benny, M, Rao, SB, Enhancing the Absorption of Curcuminoids, Spice India; 23-26 (2005).
Benny, M, Antony, B, Bioavailability of Biocurcumax™ (BCM-095™), Spice India;11-15,(2006).
Antony, B, Merina, B, Iyer, VS, Judy, N, Lennertz, K, Joyal, S, A pilot cross-over study to evaluate human oral bioavailability of BCM-95® CG (Biocurcumax™), a novel bioenhanced preparation of curcumin, Indian journal of pharmaceutical sciences, 70(4):445(2008).

\* cited by examiner

TABLE 1: PERCENTAGE INHIBITION OF INFLAMMATION IN CARRAGEENAN INDUCED PAW OEDEMA MODEL

| GROUPS | | DOSE | 30MIN | 1HR | 3HR | 6HR | 8HR | 24HR |
|---|---|---|---|---|---|---|---|---|
| GROUP 1 | VEHICLE CONTROL | 1%T80 | 0 | 0 | 0 | 0 | 0 | 0 |
| GROUP 2 | DICLOFENAC | 10mg/kg | -10.1266% | -2.64901% | 44.01914% | 37.23958% | 32.58427% | 33.52601% |
| GROUP 3 | REGULAR TURMERIC EXTRACT | 20mg/kg | -51.89% | -19.8675% | -76.555% | -49.115% | -42.6966% | -10.4046% |
| GROUP 4 | REGULAR TURMERIC EXTRACT BLENDED WITH ESSENTIAL OIL OF TURMERIC HAVING 45% AR-TURMERONE IN 10:1 RATIO | 20mg/kg | 20.8324% | 10.6375% | 44.4621% | 39.4358% | 43.21732% | 35.3942% |
| GROUP 5 | CURCUMINOID MIXTURE (C:D:B IN 0.9:1:1.1 w/w RATIO) ALONE | 20mg/kg | -31.22% | -10.31% | -21.32% | -12.65326% | -16.88325 | -1.75163% |
| GROUP 6 | CURCUMINOID(C:D:B IN 0.9: 1:1.1 w/w RATIO) BLENDED WITH EOT (HAVING 45% AR-TURMERONE) IN 10:1 RATIO | 20mg/kg | 25.31646% | 16.55629% | 41.05263% | 46.35417% | 53.74532% | 38.52601% |
| GROUP 7 | CURCUMINOID MIXTURE (C:D:B IN 0.9:1:1.1 w/w RATIO) BLENDED WITH EOT (HAVING 45% AR-TUR-MERONE) IN 12:1 RATIO | 20mg/kg | 28.32185% | 20.55416% | 51.25264% | 50.25632% | 58.22586% | 39.12155% |

*Figure 1*

TABLE 5: BIOAVAILABILITY OF CURCUMIN, DEMETHOXYCURCUMIN AND BISDEMETHOXYCURCUMIN IN HUMANS

| TIME IN HRS | REGULAR TURMERIC EXTRACT | | | REGULAR TURMERIC EXTRACT BLENDED WITH EOT HAVING 45% AR-TURMERONE IN 10:1 RATIO | | | CURCUMINOIDS HAVING C:D:B IN 0.9:1:1.1 w/w RATIO | | | CURCUMINOIDS (C:D:B IN 0.9:1:1.1 w/w RATIO) BLENDED WITH EOT HAVING 45% AR-TURMERONE IN 10:1 RATIO | | | CURCUMINOIDS (C:D:B IN 0.9:1:1.1 w/w RATIO) BLENDED WITH EOT HAVING 45% AR-TURMERONE IN 12:1 RATIO | | |
|---|---|---|---|---|---|---|---|---|---|---|---|---|---|---|---|
| | C IN ng/g | DMC IN ng/g | BDMC IN ng/g | C IN ng/g | DMC IN ng/g | BDMC IN ng/g | C IN ng/g | DMC IN ng/g | BDMC IN ng/g | C IN ng/g | DMC IN ng/g | BDMC IN ng/g | C IN ng/g | DMC IN ng/g | BDMC IN ng/g |
| 0 | 0 | 0 | 0 | 0 | 0 | 0 | 0 | 0 | 0 | 0 | 0 | 0 | 0 | 0 | 0 |
| 0.5 | 3.5 | ND | ND | 6.85 | ND | ND | 2.2 | 1.3 | 1.6 | 20.3 | 26.5 | 39.6 | 25.6 | 40.1 | 51.2 |
| 1 | 9.3 | ND | ND | 15.23 | ND | ND | 10.8 | 2.2 | 2.3 | 35.8 | 45.4 | 56.1 | 43.4 | 61.6 | 72.5 |
| 1.5 | 5.3 | ND | ND | 14.84 | ND | ND | 4.2 | 3.6 | 3.5 | 61.5 | 72.5 | 89.4 | 83.5 | 79.5 | 98.2 |
| 2 | 15.3 | ND | ND | 21.95 | ND | ND | 13.9 | 2.6 | 3.2 | 90.2 | 99.5 | 112.4 | 103.9 | 103.2 | 117.3 |
| 2.5 | 12.3 | ND | ND | 93.56 | ND | ND | 10.8 | 3.5 | 1.6 | 98.2 | 114.6 | 132.9 | 112.7 | 121.9 | 136.7 |
| 3 | 7.3 | ND | ND | 19.8 | ND | ND | 5.3 | 2.2 | 2.2 | 102.6 | 120.2 | 140.7 | 118.1 | 125.1 | 152.5 |
| 4 | 9.1 | ND | ND | 24.33 | ND | ND | 7.3 | 1.2 | 1.1 | 92.4 | 103.3 | 119.6 | 97.9 | 114.9 | 129.7 |
| 6 | 2.3 | ND | ND | 8.43 | ND | ND | 3.5 | 1.3 | 1.0 | 86.2 | 96.4 | 105.1 | 88.5 | 104.6 | 115.2 |
| 8 | 1.6 | ND | ND | 5.09 | ND | ND | ND | ND | ND | 71.5 | 84.1 | 96.4 | 79.9 | 89.1 | 102.9 |
| 10 | ND | ND | ND | ND | ND | ND | ND | ND | ND | 68.6 | 76.8 | 83.8 | 73.9 | 79.7 | 85.8 |

*Figure 2*

FORMULATION OF CURCUMINOIDS WITH ENHANCED BIOAVAILABILITY OF CURCUMIN, DEMETHOXYCURCUMIN, BISDEMETHOXYCURCUMIN AND METHOD OF PREPARATION AND USES THEREOF

This application is a continuation of co-pending U.S. patent application Ser. No. 15/288,882 filed Oct. 7, 2016, which is a divisional of U.S. patent application Ser. No. 14/206,044 filed Mar. 12, 2014, which is a non-provisional of U.S. patent application Ser. No. 61/794,175 filed Mar. 15, 2013; and U.S. patent application Ser. No. 15/288,882 is a continuation-in-part of U.S. patent application Ser. No. 14/520,292 filed Oct. 21, 2014;

this Application is a continuation-in-part of U.S. patent application Ser. No. 15/478,013 filed Apr. 3, 2017, which is a continuation of U.S. patent application Ser. No. 14/476,555 filed Sep. 3, 2014, which is a divisional of U.S. patent application Ser. No. 13/645,031 filed Oct. 4, 2012, which is a continuation-in-part of PCT/IN11/00232 filed Apr. 4, 2011, which claims priority of Indian Provisional Application Serial No. 950/CHE/2010, filed Apr. 5, 2010; and, U.S. patent application Ser. No. 15/478,013 is a continuation-in-part of U.S. patent application Ser. No. 14/520,292 filed Oct. 21, 2014;

this application is a continuation-in-part of U.S. patent application Ser. No. 15/844,459 filed Dec. 15, 2017, which a continuation of U.S. patent application Ser. No. 14/623,608 filed Feb. 17, 2015, which is a divisional of U.S. patent application Ser. No. 13/674,249 filed Nov. 12, 2012, which is a divisional of U.S. patent application Ser. No. 13/506,572 filed Apr. 30, 2012, which is a divisional of U.S. patent application Ser. No. 12/926,980 filed Dec. 21, 2010, which is a divisional of U.S. patent application Ser. No. 12/073,864 filed Mar. 11, 2008, which is a continuation-in-part of U.S. patent application Ser. No. 11/635,599 filed Dec. 8, 2006, which is a continuation of PCT/IN05/00176 filed May 30, 2005;

this application is a continuation-in-part of U.S. patent application Ser. No. 15/689,442 filed Aug. 29, 2017, which is a continuation of U.S. patent application Ser. No. 14/520,292 filed Oct. 21, 2014, which is a divisional of U.S. patent application Ser. No. 14/094,725 filed Dec. 2, 2013, which is a divisional of U.S. patent application Ser. No. 13/385,717 filed Mar. 5, 2012, which is a divisional of U.S. patent application Ser. No. 12/926,985 filed Dec. 21, 2010, which is a divisional of U.S. patent application Ser. No. 12/662,740 filed Apr. 30, 2010, which is a divisional of U.S. patent application Ser. No. 11/635,599 filed Dec. 8, 2006, Which is a continuation of PCT/IN05/00176 filed May 30, 2005;

this application is a continuation-in-part of U.S. patent application Ser. No. 14/698,944 filed Apr. 29, 2015, which is a continuation of PCT/IN13/00673 filed Oct. 31, 2013, which claims priority of Indian Provisional Appl. Ser. No. INDIA 4128/CHE/2012 filed Nov. 3, 2012 and, U.S. application Ser. No. 14/698,944 is a continuation-in-part of U.S. patent application Ser. No. 14/623,608 filed Feb. 17, 2015, which is a divisional of U.S. patent application Ser. No. 13/674,249 filed Nov. 12, 2012, which is a divisional of U.S. patent application Ser. No. 13/506,572 filed Apr. 30, 2012, which is a divisional of U.S. patent application Ser. No. 12/926,980 filed Dec. 21, 2010, which is a divisional of U.S. patent application Ser. No. 12/073,864 filed Mar. 11, 2008, which is a continuation-in-part of U.S. patent application Ser. No. 11/635,599 filed Dec. 8, 2006, which is a continuation of PCT/IN05/00176 filed May 30, 2005;

this application is a continuation-in-part of U.S. patent application Ser. No. 14/800,950 filed Jul. 16, 2015, which is a continuation of PCT/IN14/00031 filed Jan. 16, 2014, which claims priority of Indian Provisional Application Ser. No. INDIA 226/CHE/2013 filed Jan. 17, 2013 and, U.S. application Ser. No. 14/800,950 is a continuation-in-part of U.S. patent application Ser. No. 14/698,944 filed Apr. 29, 2015, which is a continuation-in-part of U.S. patent application Ser. No. 14/623,608 filed Feb. 17, 2015, which is a divisional of U.S. patent application Ser. No. 13/674,249 filed Nov. 12, 2012, which is a divisional of U.S. patent application Ser. No. 13/506,572 filed Apr. 30, 2012, which is a divisional of U.S. patent application Ser. No. 12/926,980 filed Dec. 21, 2010, which is a divisional of U.S. patent application Ser. No. 12/073,864 filed Mar. 11, 2008, which is a continuation-in-part of U.S. patent application Ser. No. 11/635,599 filed Dec. 8, 2006, which is a continuation of PCT/IN05/00176 filed May 30, 2005, all of which applications are incorporated in entirety by reference.

FIELD OF INVENTION

Disclosure relates to a formulation of curcuminoid mixture and essential oil of turmeric having 45% Ar-turmerone. The formulation gives enhanced bioavailability of bisdemethoxycurcumin, demethoxycurcumin in addition to curcumin for up to 10 hrs. The curcuminoid mixture comprises curcumin, demethoxycurcumin and bisdemethoxycurcumin in which curcumin ranges from about 0.8 to about 1.0 part weight/weight, demethoxy curcumin ranges from about 1.0 to about 1.1 part weight/weight and bisdemethoxy curcumin ranges from about 1.0 to about 1.2 part weight/weight. In the curcuminoid mixture the ratio of curcumin, demethoxy curcumin and bisdemethoxy curcumin ranges from about 0.8:1:1 to about 1:1.1:1.2 weight/weight ratio. The formulation provides improved biological activity and bioavailability of curcumin, demthoxycurcumin and bisdemethoxycurcumin.

BACKGROUND OF THE INVENTION

Turmeric is a spice grown in India and other tropical regions of Asia. It has a long history of use in herbal remedies, particularly in China, India, and Indonesia. Turmeric or "yellow root" is a general term for plants and plant materials having a high content of curcuminoids, compounds that have a strong colouring effect and which are used extensively in the colouring of e.g. food products.

Curcumin, reddish orange and with two methoxy groups, is the principal curcuminoid of the popular Indian spice turmeric, which is a member of the ginger family (Zingiberaceae). Turmeric's other two curcuminoids are demethoxycurcumin, orange-yellow with one methoxy group, and bisdemethoxycurcumin, yellow and without a methoxy group. The curcuminoids are natural phenols that are responsible for the yellow color of turmeric.

Preparing solvent extracts of Curcuma plant materials, in particular rhizomes, provides an oleoresin comprising an essential oil of turmeric and curcuminoids. The oleoresin may subsequently be subjected to a crystallization step resulting in the obtainment of curcuminoid crystals of a relatively high purity and a liquid part. Liquid part included essential oil of turmeric, flavouring compounds, any impurities that remained in solution and, curcuminoids that did not crystallize. Essential oil of turmeric is isolated from the liquid part by steam distillation. The residual material that remains after the above separation of curcuminoid crystals and essential oil of turmeric consists mainly of uncrystallized curcuminoids. This residue is generally disposed of as a waste product of the industrial process.

SUMMARY

The disclosure provides a composition for enhanced bioavailability of curcumin, demethoxycurcumin and bisdemethoxycurcumin. The composition includes a curcuminoid mixture and essential oil of turmeric. The curcuminoid mixture includes curcumin, demethoxycurcumin and bisdemethoxycurcumin in a weight ratio of curcumin:demethoxycurcumin:bisdemethoxycurcumin of about 0.8:1:1 to about 1:1.1:1.2. The essential oil of turmeric includes about 45% Ar-turmerone. The weight ratio of the curcuminoid mixture to essential oil of turmeric ranges from about 1:3 to about 99:1. In some embodiments the weight ratio of the curcuminoid mixture to essential oil of turmeric ranges is about 10:1. In some embodiments the weight ratio of the curcuminoid mixture to essential oil of turmeric ranges is about 12:1.

The disclosure provides a formulation which gives enhanced bioavailability of bisdemethoxycurcumin, demethoxycurcumin, and curcumin for up to 10 hrs.

Disclosure provides a process for obtaining curcuminoid mixture with curcumin, demethoxycurcumin and bisdemethoxycurcumin blended with essential oil of turmeric having 45% Ar-turmerone. More specifically, the disclosure provides a process wherein the residue, previously considered as a waste obtained after the separation of essential oil and curcuminoids from oleoresin, is made useful by a silica impregnation method. The process results a curcuminoid mixture having curcumin, demethoxycurcumin and bisdemethoxycurcumin in 0.8:1:1 to 1:1.1:1.2 weight/weight ratio.

In some embodiments, the ratio of the three curcuminoid mixture obtained from waste obtained after the separation of essential oil and curcuminoids from oleoresin is about 10-90% of curcumin, about 6-70% of demethoxycurcumin and about 2-60% of bisdemethoxycurcumin.

BRIEF DESCRIPTION OF THE DRAWINGS

FIG. 1 provides Table 1. Table 1 shows percentage inhibition of inflammation in carrageenan induced paw oedema model.

FIG. 2 provides Table 5. Table 5 provides bioavailability of curcumin, demethoxycurcumin and bisdemethoxycurcumin in human subjects following by administration of different extracts.

DETAILED DESCRIPTION

The disclosure provides a process wherein the residue, previously considered as a waste obtained after the separation of essential oil and curcuminoids from oleoresin, is made useful by a silica impregnation method. The process results a curcuminoid mixture having curcumin, demethoxycurcumin and bisdemethoxycurcumin in about 0.8:1:1 to about 1:1.1:1.2 weight/weight ratio. The disclosure provides a formulation of curcuminoid mixture having curcumin, demethoxycurcumin and bisdemethoxycurcumin in 0.8:1:1 to 1:1.1:1.2 weight/weight ratio and an essential oil of turmeric having 45% Ar-turmerone. The formulation gives enhanced bioavailability of bisdemethoxycurcumin, demethoxycurcumin in addition to curcumin for up to 10 hrs.

In some embodiments, the formulation provides a curcuminoid mixture having curcumin, demethoxycurcumin and bisdemethoxycurcumin ranging from about 0.8:1:1 to about 1:1.1:1.2 of a weight/weight ratio of curcumin:demethoxycurcumin:bisdemethoxycurcumin. This range of weight ratio of the curcumin, demethoxycurcumin and bisdemethoxy curcumin is obtained by extraction of the curcumin from a turmeric waste residue obtained after the extraction of curcuminoid crystals from turmeric rhizomes. The turmeric waste residue is obtained after the separation of essential oil and curcuminoid crystals from turmeric oleoresin. Curcuminoid mixture having curcumin, demethoxycurcumin and bisdemethoxycurcumin in 0.8:1:1 to 1:1.1:1.2 weight/weight ratio when blended with essential oil of turmeric having 45% Ar-turmerone gives a formulation having improved biological activity and bioavailability of curcumin, demethoxycurcumin and bisdemethoxycurcumin, as compared to biological activity and bioavailability of a formulation having curcuminoid crystals alone, or a formulation having curcuminoid crystals blended with 45% Ar-turmerone, or a formulation of curcuminoid mixture alone having a weight ratio of curcumin:demethoxycurcumin:bisdemethoxycurcumin ranging from about 0.8:1:1.

In one embodiment, the ratio of the three curcuminoid mixture obtained from waste after the separation of essential oil and curcuminoids from oleoresin is typically: about 10-90% curcumin, about 6-70% demethoxycurcumin and about 2-60% bisdemethoxycurcumin.

The volatile oil of turmeric was isolated by conventional methods of steam distillation to isolate essential oils and is well known in the art.

Curcuminoids are isolated from waste or residue material. The waste or residue material is obtained after the separation of essential oil and curcuminoids from oleoresin, by silica impregnation method. The waste or residue material is passed through a silica column. The silica column is washed with methanol to obtain three methanol fractions. Methanol fractions 2 and 3 have a mixture of curcuminoids. The combination of methanol fractions 2 and 3 provides a curcuminoid mixture having curcumin, demethoxycurcumin and bisdemethoxycurcumin in a 0.8:1:1 to 1:1.1:1.2 weight/weight ratio of curcumin:demethoxycurcumin:bisdemethoxycurcumin.

Curcuminoid mixture and volatile oils of turmeric having 45% Ar-turmerone are mixed and blended to get a uniform product. The product has curcuminoid mixture in 0.8:1:1 to 1:1.1:1.2 weight/weight ratio of curcumin to demethoxycurcumin to bisdemethoxycurcumin.

The disclosure provides a method of extracting curcuminoid mixture in 0.8:1:1 to 1:1.1:1.2 weight/weight ratio of curcumin:demethoxycurcumin:bisdemethoxycurcumin from residue or waste after the separation of essential oil and curcuminoids from oleoresin of turmeric. The disclosure provides a method of extracting curcuminoid mixture from residue or waste after the separation of essential oil and curcuminoid crystals from oleoresin of turmeric. The disclosure provides a concentrated solution prepared by solvent treatment of dried turmeric rhizomes. This concentrated solution is also referred to as oleoresin. Curcuminoids are crystallized from the oleoresin, leaving behind a waste liquid which contains essential oil. It is found that the waste liquid contains essential oil also contains curcuminoids, however in industrial process the liquid can be referred to as "waste" as far as curcuminoid extraction is concerned because the liquid is discarded with no further extraction of curcuminoids is performed from this liquid. The disclosure provides a method to extract essential oil of turmeric from this liquid industrial waste. The disclosure provides a method for extracting the curcuminoids from this liquid industrial waste. The disclosure provides a method of steam distilling essential oils from the waste liquid. After steam distillation of essential oil from the waste liquid, a residue is obtained. This waste residue is discarded as industrial waste. The disclosure provides a method to extract curcuminoids having a weight/weight ratio of curcumin:demethoxycurcumin:bisdemethoxycurcumin ranging from about 0.8:1:1 to about 1:1.1:1.2 from the waste residue.

In some embodiments of the method of preparing curcuminoid mixture having a weight/weight ratio of curcumin:demethoxycurcumin:bisdemethoxycurcumin ranging from about 0.8:1:1 to about 1:1.1:1.2, rhizomes of turmeric are dried to form dried turmeric rhizomes. The dried turmeric rhizomes are powdered to form a dried turmeric rhizome powder. Ethyl acetate is added to the dried turmeric rhizome powder to obtain an ethyl acetate extract solution and a residue. The residue is separated from the ethyl acetate extract solution. The ethyl acetate extract solution is filtered. The solvent is stripped from the filtered ethyl acetate extract solution to form an ethyl acetate extract. The ethyl acetate extract is cooled to obtain crystals of curcuminoid and a liquid. The liquid includes essential oil of turmeric and curcuminoids that did not crystallize. The liquid is steam distilled to obtain essential oil of turmeric and a waste residue (also referred to as waste residue 2). The waste residue 2 is loaded onto a silica column. The silica column is washed with methanol. Three fractions of methanol eluate are collected and referred to as Fraction 1, Fraction 2 and Fraction 3. Fraction 2 and Fraction 3 are combined to obtain a combined methanol fraction. The combined methanol fraction is concentrated under heat and vacuum to obtain a concentrated methanol fraction. The concentrated methanol fraction is dried to obtain a dried methanol extract. The dried methanol extract is powdered to obtain a powder having a curcuminoid mixture of curcumin, demethoxycurcumin and bisdemethoxycurcumin in a weight ratio of curcumin:demethoxycurcumin:bisdemethoxycurcumin of about 0.8:1:1 to about 1:1.1:1.2. In some embodiments of the method, other solvents including acetone, hexane, ethyl acetate and combinations thereof can be used instead of only the ethyl acetate solvent described above.

The essential oil is fractionated to obtain three fractions. One of the fractions contains essential oil of turmeric having 45% Ar-turmerone.

The disclosure provides a method of preparing a formulation of curcuminoids in 0.8:1:1 to 1:1.1:1.2 weight/weight ratio of curcumin:demethoxycurcumin:bisdemethoxycurcumin and essential oil of turmeric having 45% Ar-turmerone. The curcuminoid mixture of curcumin, demethoxycurcumin and bisdemethoxycurcumin in a weight ratio of curcumin:demethoxycurcumin:bisdemethoxycurcumin of about 0.8:1:1 to about 1:1.1:1.2, is suspended in water to form a suspension. Essential oil having 45% Ar-turmerone is added to the suspension to form a mixture. The mixture is homogenized to form slurry. The slurry is dried under heat and vacuum to form a uniform blend of formulation. The formulation has curcuminoid mixture in 0.8:1:1 to 1:1.1:1.2 weight/weight ratio of curcumin:demethoxycurcumin:bisdemethoxycurcumin and an essential oil of turmeric having 45% Ar-turmerone. The slurry can be dried under heat and vacuum using, for example, a vaccumized desolventiser having a stirrer.

In one embodiment, a homogeneous mixture of curcuminoid mixture and water is prepared by suspending the curcuminoid mixture in about 3 to 5 times its quantity of water to form a suspension. The suspension is homogenized to obtain slurry. The slurry is dried under heat and vacuum to form a formulation having a homogeneous mixture of the curcuminoid mixture and water.

The disclosure provides a dosage form of the formulation of curcuminoids in 0.8:1:1 to 1:1.1:1.2 weight/weight ratio of curcumin:demethoxycurcumin:bisdemethoxycurcumin and essential oil of turmeric having 45% Ar-turmerone. The disclosure provides a dosage form of the formulation of curcuminoids in 0.8:1:1 to 1:1.1:1.2 weight/weight ratio of curcumin:demethoxycurcumin:bisdemethoxycurcumin and essential oil of turmeric having 45% Ar-turmerone for oral administration. Dosage forms of the formulation are selected from the group consisting of the hard gelatin capsule, soft gelatin capsule, tablet, sachet, powder, paste, solution, suspension, emulsion, pills etc.

The disclosure provides a method of preparing a gelatin capsule having curcuminoids in 0.8:1:1 to 1:1.1:1.2 weight/weight ratio of curcumin:demethoxycurcumin:bisdemethoxycurcumin and essential oil of turmeric having 45% Ar-turmerone by suspending curcuminoid mixture in water to form a suspension. Then essential oil turmeric is added to the suspension to form a mixture. Then the mixture is homogenized to obtain a slurry. Then the slurry is dried under heat and vacuum to form a uniform blend of a composition having the curcuminoid and the essential oil of turmeric. Then the blend is filled into a gelatin capsule. Gelatin capsules are prepared by a capsule filling machine manufactured by Pam Pharmaceuticals, Mumbai, India.

In some embodiments, the weight ratio of the curcuminoid mixture, which has a 0.8:1:1 to 1:1.1:1.2 weight/weight ratio of curcumin:demethoxycurcumin:bisdemethoxycurcumin, to the essential oil of turmeric ranges from about 1:1 to about 90:1. The curcuminoid mixture having curcumin:demethoxycurcumin:bisdemethoxycurcumin in a 0.8:1:1 to 1:1.1:1.2 weight/weight ratio is also referred to as curcuminoid mixture. In some embodiments, the weight ratio of the curcuminoid mixture to the essential oil of turmeric ranges from about 1:1 to about 3:1. The weight ratio of the curcuminoid mixture to the essential oil of turmeric can be varied from about 3:1 to about 99:1. In some embodiments, the weight ratio of the curcuminoid mixture to the essential oil of turmeric ranges from about 1:1 to about 70:1. In some embodiments, the weight ratio of the curcuminoid mixture to the essential oil of turmeric ranges from about 1:1 to about 45:1. In some embodiments, the weight ratio of the curcuminoid mixture to the essential oil of turmeric ranges from about 3:1 to about 50:1. In some embodiments, the weight ratio of the curcuminoid mixture to the essential oil of turmeric ranges from about 8:1 to about 25:1. In some embodiments, the weight ratio of the curcuminoid mixture to the essential oil of turmeric is about 90:7. In some embodiments, the weight ratio of the curcuminoid mixture to the essential oil of turmeric is about 90:8. In some embodiments, the weight ratio of the curcuminoid mixture to the essential oil of turmeric is about 90:9. In some embodiments, the weight ratio of the curcuminoid mixture to the essential oil of turmeric is about 89:9. In some embodiments, the weight ratio of the curcuminoid mixture to the essential oil of turmeric is about 89:8. In one embodiment, the ratio is about 85:15. In another embodiment, the ratio is about 92:8. In another embodiment, the ratio is about 95:5. In another embodiment the weight ratio is about 10:1. In some embodiments, the weight ratio is about 12:1. In some embodiments, the weight ratio of the curcuminoid mixture to the essential oil of turmeric is about 1:2. In some embodiments, the weight ratio of the curcuminoid mixture to the essential oil of turmeric is about 2:1. In some embodiments, the weight ratio of the curcuminoid mixture to the essential oil of turmeric ranges from about 1:3 to about 99:1.

Some embodiments provide a method of enhancing bioavailability of curcumin by administering the formulation of curcuminoid mixture and essential oil of turmeric. Some embodiments provide a method of enhancing bioavailability of demethoxycurcumin by administering the composition of curcuminoid mixture and essential oil of turmeric. Some embodiments provide a method of enhancing bioavailability of bisdemethoxycurcumin by administering the composition of curcuminoid mixture and essential oil of turmeric. Some embodiments provide a method of enhancing bioavailability of curcumin, demethoxy curcumin and bisdemethoxy curcumin in a tissue by administering the composition of curcuminoid mixture and essential oil of turmeric. Enhancement of bioavailability of curcumin is observed in tissues including lungs, heart, kidney, brain, liver, pancreas, stomach, intestine and skin. Enhancement of bioavailability of demethoxy curcumin is observed in tissues including lungs, heart, kidney, brain, liver, pancreas, stomach, intestine and skin. Enhancement of bioavailability of bisdemethoxy curcumin is observed in tissues including lungs, heart, kidney, brain, liver, pancreas, stomach, intestine and skin.

Another embodiment of the present invention provides a formulation having a curcuminoid mixture in 0.9:1:1.1 weight/weight ratio of curcumin:demethoxycurcumin:bisdemethoxycurcumin and a ratio of curcuminoid mixture: essential oil of turmeric of about 10:1 or about 12:1 ratio. The essential oil of turmeric includes 45% Ar-turmerone. The formulation has anti-inflammatory activity.

Inflammation is a complex biological response of vascular tissues and immune cells to harmful stimuli, such as pathogens, damaged cells, or irritants. It is characterized by five signs: redness, increased heat, swelling, pain, and/or loss of function. Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process. At present, the majority of medicines widely used as anti-inflammatory agents are nonsteroid anti-inflammatory drugs (NSAIDs) that have, as the mechanism of action, an inhibitory action on cyclooxygenases (COXs) that is involved in the biosynthesis of prostanoids. However, since prostanoid synthesis activity is present in various tissues in the living body and governs the homeostasis thereof, various side effects are induced when NSAID is administered. One test for inflammation is the C-reactive protein (CRP) measurement. Some clinicians are advocating including it routinely. The CRP test detects any inflammation, no matter where it is. A skinned knee, flu, arthritis and infections are common causes of elevated CRP. Anti-inflammatory activity of extracts/drugs can be evaluated in small animals like rats and mice. A classic model is carrageenan induced paw oedema model in rats. Carrageenan is an irritant and produces inflammation in rats paw after injecting a small volume into sub-plantar region. The volume of paw increases within 30 minutes of injecting carrageenan which can be measured by a plethysmometer. Volume of paw should be measured at various time points after carrageenan and test drug administration and should be compared with control.

An anti-inflammatory activity of formulation having a curcuminoid mixture in about a 0.9:1:1.1 weight/weight ratio of curcumin:demethoxycurcumin:bisdemethoxycurcumin (C:D:B) and essential oil of turmeric having 45% Ar-turmerone in about a 10:1 and about 12:1 ratios showed higher percentage inhibition of inflammation. A higher value of percentage inhibition indicates more anti-inflammatory activity. Whereas curcuminoid mixture having C:D:B in 0.9:1:1.1 w/w ratio and regular turmeric extract showed negative percentage inhibition of inflammation. A negative percentage inhibition indicates that test material did not showing anti-inflammatory effect. Formulation of curcuminoid mixture having C:D:B in 0.9:1:1.1 ratio blended with essential oil of turmeric having 45% Ar-turmerone in 10:1 or in 12:1 ratios shows a decrease in inflammation from about 30 mins to about 24 hours.

Some embodiments provide a composition to decrease inflammation. The composition includes a curcuminoid mixture and essential oil of turmeric. The curcuminoid mixture includes curcumin, demethoxycurcumin and bisdemethoxycurcumin in a weight ratio of curcumin:demethoxycurcumin:bisdemethoxycurcumin of about 0.8:1:1 to about 1:1.1:1.2. The essential oil of turmeric includes about 45% Ar-turmerone. Some embodiments provide a method to decrease inflammation by administering the composition of curcuminoid mixture and essential oil of turmeric. In some embodiments, the decrease in inflammation is observed from about 30 mins to about 24 hours following administration of the composition of curcuminoid mixture and essential oil of turmeric.

Some embodiments provide a composition to decrease swelling. The composition includes a curcuminoid mixture and an essential oil of turmeric. The curcuminoid mixture includes curcumin, demethoxycurcumin and bisdemethoxycurcumin in a weight ratio of curcumin:demethoxycurcumin:bisdemethoxycurcumin of about 0.8:1:1 to about 1:1.1:1.2. The essential oil of turmeric includes about 45% Ar-turmerone. Some embodiments provide a method of decreasing swelling by administering the composition of curcuminoid mixture and essential oil of turmeric.

In some embodiments of the formulation having curcuminoid mixture having C:D:B in 0.9:1:1.1 ratio blended with essential oil of turmeric having 45% Ar-turmerone in 10:1 or in 12:1 ratios, enhances bioavailability of curcumin, demethoxycurcumin and bisdemethoxycurcumin in the body tissues.

In another embodiment, the formulation of curcuminoid mixture having C:D:B in 0.9:1:1.1 ratio blended with essential oil of turmeric having 45% Ar-turmerone in 10:1 or in 12:1 ratios, enhances the bioavailability of curcumin, demethoxycurcumin and bisdemethoxycurcumin in the blood for up to 10 hrs. After administering capsules having a 10:1 weight ratio of curcuminoid mixture having C:D:B in 0.9:1:1.1 w/w ratio blended with essential oil of turmeric having 45% Ar-turmerone, the maximum absorption for curcumin was 102.6 ng/gm, for demethoxycurcumin 120.2 ng/gm and for bisdemethoxycurcumin 140.7 ng/gm. After administering capsules having a 12:1 weight ratio of curcuminoid mixture having C:D:B in 0.9:1:1.1 w/w ratio blended with essential oil of turmeric having 45% Ar-turmerone, the maximum absorption for curcumin was 118.1 ng/gm, for demethoxycurcumin 125.1 ng/gm and for bisdemethoxycurcumin 152.5 ng/gm. Treating subjects with curcuminoid mixture having C:D:B in 0.9:1:1.1 w/w ratio shows low detection of curcumin, demethoxycurcumin and bisdemethoxycurcumin.

EXAMPLES

Example 1

Method of Preparation of Regular Turmeric Extract

The rhizomes of turmeric (500 Kg) were dried. The dried turmeric rhizomes were powdered to form powdered turmeric. Ethyl acetate extraction of the powdered turmeric was performed. For the extraction, ethyl acetate (1500 L) was added to the powdered turmeric at 78° C. temperature for 1 hr. After ethyl acetate extraction a solution and a residue 1 were obtained. The residue 1 was separated from the solution and 1500 liters of ethyl acetate was again added to the residue 1 for extraction at 78° C. temperature for 1 hr. The resultant residue was similarly extracted with ethyl acetate for three more times. The solution from each of the ethyl acetate extraction steps was combined and filtered. The solvent from the filtered solution was stripped to form an extract. Then the extract was cooled to about 4° C. to obtain crystals of curcuminoid (20 Kg) and a liquid. The crystals of curcuminoid were isolated from the liquid by filtration. The crystal of curcuminoid included mixture of curcumin, demethoxycurcumin and bisdemethoxycurcumin. The crystals of curcuminoid were also referred to as regular turmeric extract.

Example 2

Preparation of Fractions of Essential Oil of Turmeric

The rhizomes of turmeric (500 Kg) were dried. The dried turmeric rhizomes were powdered to form powdered turmeric. Ethyl acetate extraction of the powdered turmeric was performed. For the extraction, ethyl acetate (1500 L) was added to the powdered turmeric at 78° C. temperature for 1 hr. After ethyl acetate extraction a solution and a residue 1 were obtained. The residue 1 was separated from the solution and 1500 liters of ethyl acetate was again added to the residue 1 for extraction at 78° C. temperature for 1 hr. The resultant residue was similarly extracted with ethyl acetate for three more times. The solution from each of the ethyl acetate extraction steps was combined and filtered. The solvent from the filtered solution was stripped to form an extract. Then the extract was cooled to about 4° C. to obtain crystals of curcuminoid and a liquid. The crystals of curcuminoid were isolated from the liquid by filtration. The crystal of curcuminoid included mixture of curcumin, demethoxycurcumin and bisdemethoxycurcumin. The crystals of curcuminoid were referred to as regular turmeric extract.

The liquid included essential oil of turmeric, flavouring compounds, any impurities that remained in solution, and, curcuminoids that did not crystallize. The liquid was then steam distilled to isolate essential oil of turmeric having 10-15% Ar-turmerone (25 Kg) and a residue 2. The essential oil having 10-15% Ar-turmerone was fractionated at different temperatures to obtain three fractions. Essential oil of turmeric having 45% Ar-turmerone (7.5 Kg) was obtained as fraction 3. Essential oil of turmeric having 4-5% Ar-turmerone (8.3 Kg) was obtained as fraction 2. Essential oil of turmeric having 2-3% Ar-turmerone (9.3 Kg) was obtained as fraction 1.

Example 3

Method of Preparation of Formulation Having Regular Turmeric Extract and Essential Oil of Turmeric (Having 45% Ar-Turmerone) in a 10:1 Ratio.

Regular turmeric extract (2.7 Kg) prepared as per example 1 was suspended in water (12 L) to form a suspension. From Example 2, the fraction of essential oil (fraction 3) having 45 Ar-turmerone (0.27 Kg) was added to the suspension in 10:1 ratio of regular turmeric extract:essential oil of turmeric to obtain a mixture of regular turmeric extract and essential oil of turmeric. The mixture of regular turmeric extract blended with essential oil of turmeric was pulverized in a colloidal mill to form a slurry. Water was stripped from the slurry under heat and vacuum to form a uniform blend (3 Kg) of formulation. The formulation included regular turmeric extract and essential oil of turmeric (having 45% Ar-turmerone) in 10:1 ratio.

Example 4

Preparation of Curcuminoid Mixture Having Curcumin, Demethoxycurcumin, Bisdemetoxycurcumin in a Ratio of 0.9:1:1.1.

The rhizomes of turmeric (500 Kg) were dried. The dried turmeric rhizomes were powdered to form powdered turmeric. Ethyl acetate extraction of the powdered turmeric was performed. For the extraction, ethyl acetate (1500 L) was added to the powdered turmeric at 78° C. temperature for 1 hr. After ethyl acetate extraction a solution and a residue 1 were obtained. The residue 1 was separated from the solution and 1500 liters of ethyl acetate was again added to the residue 1 for extraction at 78° C. temperature for 1 hr. The resultant residue was similarly extracted with ethyl acetate for three more times. The solution from each of the ethyl acetate extraction steps was combined and filtered. The solvent from the filtered solution was stripped to form an extract. Then the extract was cooled to about 4° C. to obtain crystals of curcuminoid and a liquid. The crystals of curcuminoid were isolated from the liquid by filtration. The crystals of curcuminoid included mixture of curcumin, demethoxycurcumin and bisdemethoxycurcumin. The crystals of curcuminoid were referred to as regular turmeric extract.

The liquid included essential oil of turmeric, flavouring compounds, any impurities that remained in solution, and, curcuminoids that did not crystallize. The liquid was then steam distilled to isolate essential oil of turmeric having 10-15% Ar-turmerone (25 Kg) and a residue 2. The essential oil having 10-15% Ar-turmerone was fractionated at different temperatures to obtain three fractions. Essential oil having 45% Ar-turmerone (7.5 Kg) was obtained as fraction 3. Essential oil of turmeric having 4-5% Ar-turmerone (8.3 Kg) was obtained as fraction 2. Essential oil of turmeric having 2-3% Ar-turmerone (9.3 Kg) was obtained as fraction 1.

Residue 2 was passed through silica column. The silica column washed with methanol and three fractions were collected. The initial 30% elute was collected as fraction 1. The next 40% elute was collected as fraction 2. The remaining was collected as fraction 3. Methanol fractions 2 and 3 were combined and concentrated at 60-70° C. under vacuum (550 mm Hg). The concentrate was finally dried in an Agitated Thin Film Drier (ATFD). Dried extract was powdered in a pulverisor to form powder of curcuminoids. The powder of curcuminoids included curcumin, demethoxycurcumin and bisdemethoxycurcumin (4 Kg) in a 0.9:1:1.1 w/w ratio of curcumin:demethoxycurcumin:bisdemethoxycurcumin (Curcumin 18 mg, Demethoxycurcumin 20 mg and Bisdemethoxycurcumin 22 mg). The powder of curcuminoids was also referred to as curcuminoid mixture having C:D:B in 0.9:1:1.1 w/w ratio.

Example 5

Method of Preparation of Formulation Having Curcuminoid Mixture and Essential Oil of Turmeric (Having 45% Ar-Turmerone) in a 10:1 Ratio.

From Example 4, the curcuminoid mixture (2.7 Kg) obtained from residue 2 was suspended in water (12 L) to form a suspension. From Example 2, the fraction of essential oil (fraction 3) having 45% Ar-turmerone (0.27 Kg) was added to the suspension in 10:1 ratio of curcuminoid mixture:essential oil of turmeric to obtain a mixture of curcuminoid mixture and essential oil of turmeric. The mixture of curcuminoid mixture blended with essential oil of turmeric was pulverized in a colloidal mill to form a slurry. Water was stripped from the slurry under heat and vacuum to form a uniform blend (3 Kg) of formulation. The formulation included curcuminoid mixture (having Curcumin 16.36 mg, Demethoxycurcumin 18.18 mg and Bisdemethoxycurcumin 20 mg) and essential oil of turmeric (having 45% Ar-turmerone) in 10:1 ratio.

Example 6

Method of Preparation of Formulation Having Curcuminoid Mixture and Essential Oil of Turmeric (Having 45% Ar-Turmerone) in a 12:1 Ratio.

From Example 4, the curcuminoid mixture (3.5 Kg) obtained from residue 2 was suspended in water (15 L) to form a suspension. From Example 2, the fraction of essential oil (fraction 3) having 45% Ar-turmerone (0.29 Kg) was added to the suspension in 12:1 ratio of curcuminoid mixture:essential oil of turmeric to obtain a mixture of curcuminoid mixture and essential oil of turmeric. The mixture of curcuminoid mixture and essential oil of turmeric was pulverized in a colloidal mill to form slurry. Water was stripped from the slurry under heat and vacuum to form a uniform blend (3.8 Kg) of formulation. The formulation included curcuminoid mixture (Curcumin 16.62 mg, Demethoxycurcumin 18.46 mg and Bisdemethoxycurcumin 20.30 mg and essential oil of turmeric (having 45% Ar-turmerone) in 12:1 ratio.

Example 7

Method of Preparation of Formulation Having Curcuminoid Mixture and Essential Oil of Turmeric (Having 45% Ar-Turmerone) in a 1:10 Ratio.

From Example 4, the curcuminoid mixture (0.27 Kg) obtained from residue 2 was suspended in water (12 L) to form a suspension. From Example 2, the fraction of essential oil (fraction 3) having 45% Ar-turmerone (2.7 Kg) was added to the suspension in 1:10 ratio of curcuminoid mixture:essential oil of turmeric to obtain a mixture of curcuminoid mixture and essential oil of turmeric. The mixture of curcuminoid mixture and essential oil of turmeric was pulverized in a colloidal mill to form a slurry. Water was stripped from the slurry under heat and vacuum to form a uniform blend (3 Kg) of formulation. The formulation included curcuminoid mixture (Curcumin 1.64 mg, Demethoxycurcumin 1.82 mg and Bisdemethoxycurcumin 2 mg) and essential oil of turmeric (having 45% Ar-turmerone) in 1:10 ratio.

Example 8

Anti-Inflammatory Activity of Curcuminoid Mixture Blended with Essential Oil of Turmeric Having 45% Ar-Turmerone Formulation of curcuminoid mixture and essential oil of turmeric having 45% Ar-turmerone were prepared in ratio of 10:1 or 12:1 ratio of curcuminoid mixture:essential oil of turmeric. The curcuminoid mixture included curcumin, demethoxycurcumin and bisdemethoxycurcumin in a 0.8:1:1 to 1:1.1:1.2 weight/weight ratio of curcumin:demethoxycurcumin:bisdemethoxycurcumin.

Anti-inflammatory activity of formulations having 10:1 and 12:1 ratio of curcuminoid mixture (C:D:B in 0.8:1:1 to 1:1.1:1.2 weight/weight ratio):essential oil of turmeric having 45% Ar-turmerone were compared with curcuminoid mixture (C:D:B in 0.8:1:1 to 1:1.1:1.2 weight/weight ratio), regular turmeric extract blended with essential oil of turmeric having 45% Ar-turmerone in 10:1 ratio or with regular turmeric extract in Wistar rats. The dosage administered for test samples was 20 mg of curcuminoids/Kg body weight of the rat. Diclofenac (standard anti-inflammatory drug) administered was 10 mg Diclofenac/Kg body weight.

Group 1 consisted of control animals and were fed with vehicle (1% Tween 80)

Group 2 consisted of animals which were given Diclofenac standard.

Dose: 10 mg Diclofenac/Kg body weight.

Group 3 animals were given regular turmeric extract having 95% curcuminoids prepared as per Example 1, of which Curcumin 15.36 mg, Demethoxycurcumin 3.42 mg and Bisdemethoxycurcumin 1.22 mg (equivalent to 20 mg curcuminoids) suspended in 1% Tween 80.

Dose: Regular turmeric extract (equivalent to 20 mg curcuminoids) suspended in 1% Tween 80/Kg body weight.

To Group 4 animals, regular turmeric extract blended with essential oil of turmeric having 45% Ar-turmerone in 10:1 ratio prepared as per Example 3 (Curcumin 13.96 mg, Demethoxycurcumin 3.11 mg and Bisdemethoxycurcumin 1.11 mg) suspended in 1% Tween 80 and fed.

Dose: Regular turmeric extract blended with essential oil of turmeric having 45% Ar-turmerone in 10:1 ratio (equivalent to 20 mg curcuminoids) suspended in 1% Tween 80/Kg body weight.

Curcuminoid mixture having C:D:B in 0.9:1:1.1 w/w ratio (prepared as per Example 4) with Curcumin 6 mg, Demethoxycurcumin 6.67 mg and Bisdemethoxycurcumin 7.33 mg was suspended in 1% Tween 80 and fed to Group 5 animals.

Dose: 20 mg Curcuminoid mixture having C:D:B in 0.9:1:1.1 w/w ratio suspended in 1% Tween 80/Kg body weight.

To Group 6 animals, curcuminoid mixture having C:D:B in 0.9:1:1.1 w/w ratio blended with essential oil of turmeric having 45% Ar-turmerone in 10:1 ratio prepared as per Example 5 suspended in 1% Tween 80 and fed.

Dose: 20 mg of the formulation (Curcumin 5.45 mg, Demethoxycurcumin 6.06 mg, Bisdemethoxycurcumin 6.9 mg and essential oil of turmeric having 45% Ar-turmerone) suspended in 1% Tween 80/Kg body weight.

To Group 7 animals, curcuminoid mixture having C:D:B in 0.9:1:1.1 w/w ratio blended with essential oil of turmeric having 45% Ar-turmerone in 12:1 ratio prepared as per Example 6 was suspended in 1% Tween 80 was fed.

Dose: 20 mg of the formulation (Curcumin 5.54 mg, Demethoxycurcumin 6.16 mg and Bisdemethoxycurcumin 6.77 mg and essential oil of turmeric having 45% Ar-turmerone in 12:1 ratio) suspended in 1% Tween 80/Kg body weight.

Vehicle (1% Tween 80), formulation having 10:1 ratio of curcuminoid mixture:essential oil of turmeric (having 45% Ar-turmerone), formulation having 12:1 ratio of curcuminoid mixture:essential oil of turmeric (having 45% Ar-turmerone), curcuminoid mixture alone, regular turmeric extract, regular turmeric extract blended with essential oil of turmeric having 45% Ar-turmerone in 10:1 ratio or diclofenac (a well known anti-inflammatory drug) were administered orally to respective groups of rats orally. Then after 30 mins, the treated rats were challenged with carrageenan (0.1 ml, 1% carrageenan suspension in 0.9% NaCl solution) by injecting to the animals in subplantar region of the hind paw. Carrageenan is a chemical known to induce inflammation in rats. The paw volume was determined for all the animals at different time intervals (base line, 1 hr, 3 hr, 6 Hr, 8 hr and 24 hr) after carrageenan injection using digital plethysmometer and the percentage inhibition of inflammation was calculated using following formula:

% inhibition=(1−D/C)×100

D—Represents the difference in paw volume from baseline in test/standard group.
C—Represents the difference in paw volume from baseline in the control group.

A higher value of percentage inhibition indicated less paw volume in the animals as compared to control animals and more anti-inflammatory activity whereas a negative percentage inhibition indicated that test material did not showing anti-inflammatory effect because the animals had more paw volume than control animals at the corresponding time points.

As seen in Table 1 (FIG. 1), at each time point the rats treated with regular turmeric extract (Group 3) did not show percentage inhibition of inflammation. The rats treated with curcuminoid mixture having C:D:B in 0.9:1:1.1 w/w ratio (Group 5) showed slightly better percentage inhibition of inflammation than Group 3. Rats treated with regular turmeric extract blended with essential oil of turmeric having 45% Ar-turmerone in 10:1 ratio (Group 4) showed better percentage inhibition of inflammation than Group 3 or Group 5 and almost comparable to rats treated with Diclofenac (Group 2). Rats treated with curcuminoid mixture having C:D:B blended with essential oil of turmeric having 45% Ar-turmerone in 10:1 (Group 6) and 12:1 (Group 7) ratios showed better percentage inhibition of inflammation than rats treated with regular turmeric extract (Group 3) or regular turmeric extract blended with essential oil of turmeric having 45% Ar-turmerone in 10:1 ratio (Group 4) or curcuminoid mixture alone having C:D:B in 0.9:1:1.1 w/w ratio (Group 5) or diclofenac (Group 2).

Example 9

Bio Availability of Curcumin, Demethoxycurcumin and Bisdemethoxycurcumin in Rabbits Rabbits weighing 2-2.5 Kg were used for the study. Animals were divided into 8 groups and 4 animals were used for each group. The animals were divided as shown in Table 2. The dosage administered was 60 mg curcuminoids/Kg body weight of the rabbit.

TABLE 2

Segregation of rabbits for experimental study.

| Group 1 | Control (Tween 80)<br>Dose: 60 mg of Tween 80/Kg body weight. |
|---|---|
| Group 2 | Regular turmeric extract prepared as per Example 1.<br>Dose: Regular turmeric extract (equivalent to 60 mg curcuminoids) solubilized in Tween 80/Kg body weight. |
| Group 3 | Regular turmeric extract blended with EOT having 45% Ar-turmerone in 10:1 ratio prepared as per Example 3.<br>Dose: Regular turmeric extract blended with EOT having 45% Ar-turmerone in 10:1 ratio (equivalent to 60 mg curcuminoids) solubilized in Tween 80/Kg body weight. |
| Group 4 | Essential oil of turmeric having 45% Ar-turmerone prepared as per Example 2.<br>Dose: 60 mg of Essential oil of turmeric having 45% Ar-turmerone solubilized in Tween 80/Kg body weight. |
| Group 5 | Curcuminoid mixture having C:D:B in 0.9:1:1.1 w/w ratio prepared as per Example 4.<br>Dose: 60 mg of Curcuminoid mixture having C:D:B in 0.9:1:1.1 w/w ratio solubilized in Tween 80/Kg body weight. |
| Group 6 | Curcuminoid mixture having C:D:B in 0.9:1:1.1 w/w ratio blended with EOT having 45% Ar-turmerone in 10:1 ratio prepared as per Example 5.<br>Dose: 60 mg of the formulation (Curcuminoid mixture having C:D:B in 0.9:1:1.1 w/w ratio blended with EOT having 45% Ar-turmerone in 10:1 ratio) solubilized in Tween 80/Kg body weight. |
| Group 7 | Curcuminoid mixture having C:D:B in 0.9:1:1.1 w/w ratio blended with EOT having 45% Ar-turmerone in 12:1 ratio prepared as per Example 6.<br>Dose: 60 mg of the formulation (Curcuminoid mixture having C:D:B in 0.9:1:1.1 w/w ratio blended with EOT having 45% Ar-turmerone in 12:1 ratio) in solubilized Tween 80/Kg body weight. |
| Group 8 | Curcuminoid mixture having C:D:B in 0.9:1: 1.1 w/w ratio blended with EOT having 45% Ar-turmerone in 1:10 ratio prepared as per Example 7.<br>Dose: 60 mg of the formulation (Curcuminoid mixture having C:D:B in 0.9:1:1.1 w/w ratio blended with EOT having 45% Ar-turmerone in 1:10 ratio) solubilized in Tween 80/Kg body weight. |

Group 1 consisted of animals which were given vehicle, Tween 80.

Group 2 animals were given regular turmeric extract (equivalent to 60 mg/kg curcuminoids dose) (curcumin control) of which Curcumin 46.11 mg, Demethoxycurcumin 10.23 mg and Bisdemethoxycurcumin 3.66 mg solubilized in Tween 80.

To Group 3 animals, regular turmeric extract blended with essential oil of turmeric having 45% Ar-turmerone in 10:1 ratio (Curcumin 41.92 mg, Demethoxycurcumin 9.3 mg and Bisdemethoxycurcumin 3.32 mg) solubilized in Tween 80 and fed at dose equivalent to 60 mg/kg curcuminoids.

To Group 4 animals, essential oil of turmeric having 45% Ar-turmerone (60 mg/kg) in Tween 80 was given.

Curcuminoid mixture (60 mg/kg) having C:D:B in 0.9:1:1.1 w/w ratio with Curcumin 18 mg, Demethoxycurcumin 20 mg and Bisdemethoxycurcumin 22 mg was solubilized in Tween 80 and fed to Group 5 animals.

To Group 6 animals, curcuminoid mixture having C:D:B in 0.9:1:1.1 w/w ratio blended with essential oil of turmeric having 45% Ar-turmerone in 10:1 ratio (Final formulation contain Curcumin 16.36 mg, Demethoxycurcumin 18.18 mg and Bisdemethoxycurcumin 20 mg and essential oil of turmeric with 45% Ar-turmerone) solubilized in Tween 80 and fed at 60 mg/kg curcuminoid dose.

To group 7 animals, curcuminoid mixture having C:D:B in 0.9:1:1.1 w/w ratio blended with essential oil of turmeric in 12:1 ratio (Final formulation contain Curcumin 16.62 mg, Demethoxycurcumin 18.46 mg, Bisdemethoxycurcumin 20.30 mg and essential oil of turmeric with 45% Ar-turmerone.) solubilized in Tween 80 was fed at 60 mg/kg of curcuminoids.

To Group 8 animals, curcuminoid mixture blended with essential oil of turmeric solubilized in Tween 80 was fed at 60 mg/kg curcuminoids. The curcuminoid mixture had a 0.9:1:1.1 w/w ratio of curcumin:demethoxycurcumin:bisdemethoxycurcumin. The essential oil of turmeric had 45% Ar-turmerone. The ratio of curcuminoid mixture:essential oil of turmeric was 1:10 (Final formulation contain Curcumin 1.64 mg, Demethoxycurcumin 1.82 mg and Bisdemethoxycurcumin 2 mg).

The study drugs were given by oral route. Two hours post drug, blood was collected from the ear vein of each rabbit for HPLC analysis of amount of curcumin, demethoxycurcumin and bisdemethoxycurcumin. The blood was extracted exhaustively with ethyl acetate to recover the above components. The ethyl acetate extract was analyzed by HPLC on a RP-C18 column (250×4.5 mm) using tetrahydrofuran (THF) as solvent and UV detection at 420 nm. The eluent flow rate was 1 ml/min. Table 3 provides the amount of curcumin, demethoxycurcumin and bisdemethoxycurcumin in nanograms per gram of blood in rabbits by administering different extracts.

(Group 5) or curcuminoid mixture blended with essential oil of turmeric having 45% Ar-turmerone in 1:10 ratio (Group 8). In group 5 rabbits fed with curcuminoid mixture having C:D:B in 0.9:1:1.1, the level of curcumin, demethoxy curcumin and bisdemethoxycurcumin was found to be 6.3±0.31, 1.5±0.44 and 2.9±0.89 respectively. Where as in Group 6 animals fed with curcuminoid mixture blended with essential oil of turmeric having 45% Ar-turmerone in 10:1, the level of curcumin, demethoxycurcumin and bisdemethoxy curcumin in blood was 91.6±2.3, 98.5±3.1, 105.8±5.2 ng/g respectively. In group 7 animals fed with curcuminoid mixture blended with essential oil of turmeric having 45% Ar-turmerone in 12:1 has shown slightly higher curcuminoid level (curcumin, demethoxycurcumin and bisdemethoxy curcumin in blood was 101.5±2.3, 107.4±2.5, 112.9±3.4 ng/g respectively) than the rabbits fed with curcuminoid mixture blended with essential oil of turmeric having 45% Ar-turmerone in 10:1 ratio. These results indicate that combining essential oil of turmeric with curcuminoid mixture having C:D:B in 0.9:1:1.1 ratio increases the blood concentration of curcuminoids to higher level. Animals fed with regular turmeric extract (Group 2) shows only low detection of curcumin (12.3±1.9 ng/gm) in blood. Demethoxycurcumin and bisdemethoxy curcumin was not detected in rabbits fed with regular turmeric extract.

TABLE 3

Bio availability of curcumin, demethoxycurcumin and bisdemethoxycurcumin in rabbits by administering different extracts.

| Groups | Treatment | Curcumin content in ng/g | Demethoxy curcumin content in ng/g | Bisdemethoxy curcumin content in ng/g |
|---|---|---|---|---|
| Group 1 | Control (Tween 80) | ND | ND | ND |
| Group 2 | Regular turmeric extract | 12.3 ± 1.9 | ND | ND |
| Group 3 | Regular turmeric extract blended with EOT having 45% Ar-t in 10:1 ratio | 45.65 ± 2.3 | ND | ND |
| Group 4 | Essential oil of turmeric having 45% Ar-turmerone | ND | ND | ND |
| Group 5 | Curcuminoid mixture having C:D:B in 0.9:1:1.1 w/w ratio | 6.3 ± 0.31 | 1.5 ± 0.44 | 2.9 ± 0.89 |
| Group 6 | Curcuminoid mixture having C:D:B in 0.9:1:1.1 w/w ratio blended with EOT having 45% Ar-t in 10:1 ratio | 91.6 ± 2.3 | 98.5 ± 3.1 | 105.8 ± 5.2 |
| Group 7 | Curcuminoid mixture having C:D:B in 0.9:1:1.1 w/w ratio blended with EOT having 45% Ar-turmerone in 12:1 ratio | 101.5 ± 2.3 | 107.4 ± 2.5 | 112.9 ± 3.4 |
| Group 8 | Curcuminoid mixture having C:D:B in 0.9:1:1.1 w/w ratio blended with EOT having 45% Ar-turmerone in 1:10 ratio | 1.3 ± 0.21 | ND | ND |

The results as shown in Table 3 indicate that curcumin, demethoxycurcumin and bisdemethoxy curcumin was detected in group 5, group 6 and group 7. The level of curcuminoids in the blood was higher in rabbits fed with curcuminoid mixture blended with essential oil of turmeric having 45% Ar-turmerone in 10:1 or in 12:1 ratios (Group 6 and 7) compared to rabbits fed with curcuminoid mixture Animals fed with regular turmeric extract blended with essential oil of turmeric having 45% Ar-turmerone in 10:1 ratio (Group 3) shows detection of curcumin (45.65±2.3 ng/gm) in blood. The curcuminoid content in the blood in animals fed with essential oil of turmeric having 45% Ar-turmerone (Group 4) was not detectable.

Example 10

Tissue Distribution Study in Rabbits

Rabbits weighing 2-2.5 Kg were used for the study. Animals were divided into 6 groups. The animals were divided as shown in Table 4. The dosage administered was 60 mg curcuminoids/Kg body weight of the rabbit.

TABLE 4

Segregation of rabbits for experimental study.

Group 1 Control (Tween 80)
  Dose: 60 mg of Tween 80/Kg body weight.
Group 2 Regular turmeric extract prepared as per Example 1.
  Dose: Regular turmeric extract (equivalent to 60 mg curcuminoids) solubilized in Tween 80/Kg body weight.
Group 3 Regular turmeric extract blended with EOT having 45% Ar-turmerone in 10:1 ratio prepared as per Example 3.
  Dose: Regular turmeric extract blended with EOT having 45% Ar-turmerone in 10:1 ratio (equivalent to 60 mg curcuminoids) solubilized in Tween 80/Kg body weight.
Group 4 Curcuminoid mixture having C:D:B in 0.9:1:1.1 w/w ratio alone prepared as per Example 4.
  Dose: 60 mg of Curcuminoid mixture having C:D:B in 0.9:1:1.1 w/w ratio solubilized in Tween 80/Kg body weight.
Group 5 Curcuminoid mixture having C:D:B in 0.9:1:1.1 w/w ratio blended with EOT having 45% Ar-turmerone in 10:1 ratio prepared as per Example 5.
  Dose: 60 mg of the formulation (Curcuminoid mixture having C:D:B in 0.9:1:1.1 w/w ratio blended with EOT having 45% Ar-turmerone in 10:1 ratio) solubilized in Tween 80/Kg body weight.
Group 6 Curcuminoid mixture having C:D:B in 0.9:1:1.1 w/w ratio blended with EOT having 45% Ar-turmerone in 12:1 ratio prepared as per Example 6.
  Dose: 60 mg of the formulation (Curcuminoid mixture having C:D:B in 0.9:1:1.1 w/w ratio blended with EOT having 45% Ar-turmerone in 12:1 ratio) solubilized in Tween 80/Kg body weight.

Group 1 consisted of animal which were given vehicle, Tween 80.

Group 2 animals were given Regular turmeric extract of which Curcumin 46.11 mg, Demethoxycurcumin 10.23 mg and Bisdemethoxy-curcumin 3.66 mg (equivalent to 60 mg curcuminoids) solubilized in Tween 80.

Group 3 animals were fed Regular turmeric extract blended with essential oil of turmeric having 45% Ar-turmerone in 10:1 ratio (Curcumin 41.92 mg, Demethoxy-curcumin 9.3 mg and Bisdemethoxycurcumin 3.32 mg) solubilized in Tween 80.

Group 4 animals were orally administered with Curcuminoid mixture having C:D:B in 0.9:1:1.1 w/w ratio with Curcumin 18 mg, Demethoxycurcumin 20 mg and Bisdemethoxycurcumin 22 mg solubilized in Tween 80.

To Group 5 animals, Curcuminoid mixture having C:D:B in 0.9:1:1.1 w/w ratio blended with essential oil of turmeric having 45% Ar-turmerone in 10:1 ratio (Final formulation contain Curcumin 16.36 mg, Demethoxycurcumin 18.18 mg, Bisdemethoxycurcumin 20 mg and essential oil of turmeric with 45% Ar-turmerone) solubilized in Tween 80 was fed.

To Group 6 animals, Curcuminoid mixture having C:D:B in 0.9:1:1.1 w/w ratio blended with essential oil of turmeric having 45% Ar-turmerone in 12:1 ratio (Final formulation contain Curcumin 16.62 mg, Demethoxycurcumin 18.46 mg, Bisdemethoxycurcumin 20.30 mg and essential oil of turmeric with 45% Ar-turmerone) solubilized in Tween 80 was fed.

The study drugs were given by oral route. Two hours post drug rabbits were sacrificed by cervical dislocation and dissected to obtain various tissues (Heart, Kidney, Brain, Liver, Pancreas, Lungs, Intestine, Stomach and Skin). Each tissue was weighed and stored in vial at −20° C. until analysis.

Tissues were homogenized and extracted with chloroform-methanol (2:1). The homogenate was filtered through a whatman filter paper and the filtrate collected and mixed thoroughly with 0.2 vol of 0.9% NaCl solution and centrifuged. The upper layer was siphoned off. The lower phase was evaporated to dryness under a stream of nitrogen at 40-45° C. in a "Turbo Vap" Concentration Work Station (Caliper Life Sciences, USA).

Dried samples of tissues were analyzed on HPLC. The dried samples were dissolved in 2 ml of acetone using a vortex mixer and analyzed by HPLC in a Shimadzu LC 20AD Liquid Chromatograph system with SPD-M20A UV detector in isocratic mode. The column used was C18 ODS Phenomenox (250×4.6 mm, 5µ particle size) using 40% tetrahydrofuran (THF), 60% water containing 1% citric acid ($P^H$ adjusted to 3 with concentrated KOH solution) as solvent system and UV detection at 420 nm. The eluent flow rate was 1 ml/min.

| | | Group 1 (Control group) | | |
|---|---|---|---|---|
| Sl No:- | Tissues | Curcumin (ng/g) | DMC | BDMC |
| 1 | Lungs | ND | ND | ND |
| 2 | Heart | ND | ND | ND |
| 3 | Kidney | ND | ND | ND |
| 4 | Brain | ND | ND | ND |
| 5 | Liver | ND | ND | ND |
| 6 | Pancreas | ND | ND | ND |
| 7 | Stomach | ND | ND | ND |
| 8 | Intestine | ND | ND | ND |
| 9 | Skin | ND | ND | ND |

| | | Group 2 - Regular turmeric extract | | |
|---|---|---|---|---|
| Sl No:- | Tissues | Curcumin ng/g | DMC ng/g | BDMC ng/g |
| 1 | Lungs | 4.2 | ND | ND |
| 2 | Heart | 17.5 | ND | ND |
| 3 | Kidney | ND | ND | ND |
| 4 | Brain | 5.3 | ND | ND |
| 5 | Liver | 10 | ND | ND |
| 6 | Pancreas | 13.4 | ND | ND |
| 7 | Stomach | 856 | ND | ND |
| 8 | Intestine | 618 | ND | ND |
| 9 | Skin | 2.1 | ND | ND |

| | | Group 3 - Regular turmeric extract blended with EOT having 45% Ar-turmerone in 10:1 ratio | | |
|---|---|---|---|---|
| Sl No:- | Tissues | Curcumin ng/g | DMC ng/g | BDMC ng/g |
| 1 | Lungs | 22.1 | ND | ND |
| 2 | Heart | 235.6 | ND | ND |
| 3 | Kidney | 21.5 | ND | ND |
| 4 | Brain | 19.6 | ND | ND |
| 5 | Liver | 87.5 | ND | ND |
| 6 | Pancreas | 223.1 | ND | ND |
| 7 | Stomach | 7456 | ND | ND |
| 8 | Intestine | 3562 | ND | ND |
| 9 | Skin | 12.4 | ND | ND |

Group 4 - Curcuminoid mixture having C:D:B in 0.9:1:1.1 w/w ratio

| Sl No:- | Tissues | Curcumin ng/g | DMC ng/g | BDMC ng/g |
|---|---|---|---|---|
| 1 | Lungs | 5.8 | ND | ND |
| 2 | Heart | 16.9 | 1.3 | ND |
| 3 | Kidney | 1.2 | ND | ND |
| 4 | Brain | 6.1 | 1.1 | ND |
| 5 | Liver | 25 | 3.4 | ND |
| 6 | Pancreas | 14.3 | 2.5 | ND |
| 7 | Stomach | 848 | 122 | ND |
| 8 | Intestine | 612 | 180 | ND |
| 9 | Skin | 1.9 | 1.1 | ND |

Group 5 - Curcuminoid mixture having C:D:B in 0.9:1:1.1 w/w ratio blended with EOT having 45% Ar-turmerone in 10:1 ratio

| Sl No:- | Tissues | Curcumin ng/g | DMC ng/g | BDMC ng/g |
|---|---|---|---|---|
| 1 | Lungs | 32.1 | 13.5 | 9.8 |
| 2 | Heart | 356.77 | 292 | 243 |
| 3 | Kidney | 29.95 | 7.2 | 12.6 |
| 4 | Brain | 29.76 | 11.7 | 8.2 |
| 5 | Liver | 122.15 | 38.26 | 22.14 |
| 6 | Pancreas | 357 | 232 | 114.5 |
| 7 | Stomach | 12135 | 10356 | 9845 |
| 8 | Intestine | 5634 | 3562 | 1123 |
| 9 | Skin | 16.2 | 9.5 | 7.2 |

Group 6 - Curcuminoid mixture having C:D:B in 0.9:1:1.1 w/w ratio blended with EOT having 45% Ar-turmerone in 12:1 ratio

| Sl No:- | Tissues | Curcumin ng/g | DMC ng/g | BDMC ng/g |
|---|---|---|---|---|
| 1 | Lungs | 40.2 | 14.8 | 16.2 |
| 2 | Heart | 402.1 | 273 | 251 |
| 3 | Kidney | 42.8 | 36.8 | 11.5 |
| 4 | Brain | 38.4 | 15.8 | 13.4 |
| 5 | Liver | 154.1 | 49.7 | 28.4 |
| 6 | Pancreas | 389.7 | 251.5 | 122.6 |
| 7 | Stomach | 15987 | 13842 | 10245 |
| 8 | Intestine | 7562 | 4563 | 1562 |
| 9 | Skin | 19.5 | 13.6 | 10.3 |

Pancreas, Heart and Liver showed a better absorption at 2 hrs after dosing curcuminoid mixture having C:D:B in 0.9:1:1.1 ratio blended with essential oil of turmeric having 45% Ar-turmerone in 10:1 or in 12:1 ratios. Kidney, lungs, skin and brain showed moderate amounts of curcumin, demethoxycurcumin and bisdemethoxycurcumin after dosing curcuminoid mixture having C:D:B in 0.9:1:1.1 ratio blended with essential oil of turmeric having 45% Ar-turmerone in 10:1 or in 12:1 ratios.

In Group 2 and 3 animals after consuming regular turmeric extract and regular turmeric extract blended with essential oil of turmeric having 45% Ar-turmerone, all the tissues showed absorption of curcumin. In the control group (Group 1) there was no absorption of curcuminoids in the tissues. All other tissues like Spleen, Uterus, Seminal Vesicle, Testis and Prostate also showed significant absorption of curcumin, demethoxycurcumin and bisdemethoxycurcumin after dosing with curcuminoid mixture having C:D:B in 0.9:1:1.1 ratio blended with essential oil of turmeric having 45% Ar-turmerone in 10:1 or in 12:1 ratios.

Example 11

Bioavailability of Curcumin, Demethoxycurcumin and Bisdemethoxycurcumin in Humans Nine healthy human volunteers aged between 25 and 45 years of age were selected for the study. They were given capsules containing Regular turmeric extract (equivalent to 2000 mg curcuminoids) prepared as per Example 1 (Curcumin 1536.84 mg, Demethoxycurcumin 341.05 mg and Bisdemethoxycurcumin 122.11 mg). Blood was drawn from the subjects at baseline, 0.5, 1, 1.5, 2, 2.5, 3, 4, 6, 8 and 10 hours post drug. The same subjects after a washout period of one week were given dose equivalent to 2000 mg curcuminoids having regular turmeric extract blended with essential oil of turmeric having 45% Ar-turmerone in 10:1 ratio prepared as per Example 3 (Curcumin 1397.1 mg, Demethoxycurcumin 310.05 mg and Bisdemethoxycurcumin 111.01 mg). Blood was drawn from the subjects at baseline, 0.5, 1, 1.5, 2, 2.5, 3, 4, 6, 8 and 10 hours post drug.

The above protocol was repeated with the following formulation also:

(1) Capsule having 500 mg of curcuminoid mixture having C:D:B in 0.9:1:1.1 w/w ratio prepared as per Example 4 (Curcumin 600 mg, Demethoxycurcumin 666.67 mg and Bis-demethoxycurcumin 733.33 mg) was administered at a dosage of 4×500 mg (equivalent to 2000 mg curcuminoids) of composition to the human subject.

(2) Capsule having 500 mg of curcuminoid mixture in 0.9:1:1.1 w/w ratio (C:D:B) blended with EOT having 45% Ar-turmerone in 10:1 ratio prepared as per Example 5 (Final formulation contain Curcumin 545.45 mg, Demethoxycurcumin 606.06 mg, Bisdemethoxycurcumin 666.6 mg and essential oil of turmeric with 45% Ar-turmerone) was administered at a dosage of 4×500 mg (equivalent to 2000 mg curcuminoids) of composition to the human subject.

(3) Capsule having 500 mg of curcuminoid mixture in 0.9:1:1.1 w/w ratio (C:D:B) blended with EOT having 45% Ar-turmerone in 12:1 ratio prepared as per Example 6 (Final formulation contain Curcumin 553.8 mg, Demethoxycurcumin 615.38 mg, Bisdemethoxycurcumin 676.92 mg and essential oil of turmeric with 45% Ar-turmerone) was administered at a dosage of 4×500 mg (equivalent to 2000 mg curcuminoids) of composition to the human subject.

The blood was extracted exhaustively with ethyl acetate to recover the Curcumin, Demethoxycurcumin and Bisdemethoxycurcumin components. The ethyl acetate extract was analyzed by HPLC on a RP-C18 column (250×4.5 mm) using tetrahydrofuran (THF) as solvent and UV detection at 420 nm. The eluent flow rate was 1 ml/min. Table 5 (FIG. 2) provides the amount of curcumin, demethoxycurcumin and bisdemethoxycurcumin in nanograms per gram of blood for the subjects by administering different extracts.

Results showed that curcumin, demethoxycurcumin and bisdemethoxycurcumin were detected in groups treated with curcuminoid mixture having C:D:B in 0.9:1:1.1 w/w ratio alone and curcuminoid mixture having C:D:B in 0.9:1:1.1 w/w ratio blended with essential oil of turmeric having 45% Ar-turmerone in 10:1 and 12:1 ratios. The curcuminoids was detected for up to 10 hr in subjects treated with curcuminoid mixture having C:D:B in 0.9:1:1.1 w/w ratio blended with essential oil of turmeric having 45% Ar-turmerone in 10:1 and 12:1 ratios. Following administration of capsules having a 10:1 weight ratio of curcuminoid mixture having C:D:B in 0.9:1:1.1 w/w ratio blended with essential oil of turmeric having 45% Ar-turmerone, the peak absorption of curcumin, demethoxycurcumin and bisdemethoxycurcumin occurred at 3 hr. The maximum absorption for curcumin was 102.6 ng/gm, for demethoxycurcumin 120.2 ng/gm and for bisdemethoxycurcumin 140.7 ng/gm in the group fed by 10:1 weight ratio of curcuminoid mixture having C:D:B in 0.9:1:1.1 w/w ratio blended with essential oil of turmeric having 45% Ar-turmerone. The subjects treated with curcuminoids having C:D:B in 0.9:1:1.1 w/w ratio blended with essential oil of turmeric having 45% Ar-turmerone in 12:1 ratio showed slightly higher curcumin, demethoxycurcumin and bisdemethoxycurcumin level at 3 hr. The maximum absorption for curcumin was 118.1 ng/gm, for demethoxycurcumin 125.1 ng/gm and for bisdemethoxycurcumin 152.5 ng/gm in the group fed by 12:1 weight ratio of curcuminoid mixture having C:D:B in 0.9:1:1.1 w/w ratio blended with essential oil of turmeric having 45% Ar-turmerone.

Subjects treated with curcuminoid mixture having C:D:B in 0.9:1:1.1 w/w ratio showed low detection of curcumin (13.9 ng/gm), demethoxycurcumin (3.6 ng/gm) and bisdemethoxycurcumin (3.5 ng/gm).

Subjects treated with curcuminoid mixture having C:D:B in 0.9:1:1.1 w/w ratio blended with essential oil of turmeric having 45% Ar-turmerone in 10:1 and 12:1 ratios has shown higher detection of curcuminoids even at 10 hrs post drug. Whereas curcuminoid mixture having C:D:B in 0.9:1:1.1 w/w ratio alone gave a low detection of curcuminoids at 6 hrs.

Demethoxycurcumin and bisdemethoxycurcumin was not detected in the subjects treated with regular turmeric extract and regular turmeric extract blended with essential oil of turmeric. The subjects treated with regular turmeric extract blended with essential oil of turmeric having 45% Ar-turmerone in 10:1 ratio showed detection of curcumin only in the blood and Cmax was found to be 93.56 ng/gm. Curcumin was detected up to 8 hr in the blood.

Subjects treated with regular turmeric extract showed only low detection of curcumin (15.3 ng/gm) in blood.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A method of decreasing inflammation comprising administering a composition for enhanced bioavailability of curcumin, demethoxycurcumin and bisdemethoxycurcumin, the composition comprising a curcuminoid mixture and essential oil of turmeric, wherein the curcuminoid mixture comprises curcumin, demethoxycurcumin and bisdemethoxycurcumin in a weight ratio of curcumin:demethoxycurcumin:bisdemethoxycurcumin of about 0.8:1:1 to about 1:1.1:1.2, wherein the essential oil of turmeric comprises about 45% Ar-turmerone, and, wherein a weight ratio of the curcuminoid mixture to essential oil of turmeric ranges from about 1:3 to about 99:1.

2. The method of decreasing inflammation of claim 1, wherein the weight ratio of the curcuminoid mixture to essential oil of turmeric is about 12:1.

3. The method of decreasing inflammation of claim 1, wherein the weight ratio of the curcuminoid mixture to essential oil of turmeric is about 10:1.

4. The method of decreasing inflammation of claim 1, wherein a decrease in inflammation is observed from about 30 mins to about 24 hours.

5. A method of enhancing bioavailability of curcumin, demethoxycurcumin and bisdemethoxycurcumin comprising administering a composition for enhanced bioavailability of curcumin, demethoxycurcumin and bisdemethoxycurcumin, the composition comprising a curcuminoid mixture and essential oil of turmeric, wherein the curcuminoid mixture comprises curcumin, demethoxycurcumin and bisdemethoxycurcumin in a weight ratio of curcumin:demethoxycurcumin:bisdemethoxycurcumin of about 0.8:1:1 to about 1:1.1:1.2, and the essential oil of turmeric comprises about 45% Ar-turmerone, and, wherein a weight ratio of the curcuminoid mixture to essential oil of turmeric ranges from about 1:3 to about 99:1.

6. The method of enhancing bioavailability of curcumin, dimethoxycurcumin and bisdemethoxycurcumin of claim 5, wherein the weight ratio of the curcuminoid mixture to essential oil of turmeric is about 12:1.

7. The method of enhancing bioavailability of curcumin, dimethoxycurcumin and bisdemethoxycurcumin of claim 5, wherein the weight ratio of the curcuminoid mixture to essential oil of turmeric is about 10:1.

8. The method of enhancing bioavailability of curcumin, dimethoxycurcumin and bisdemethoxycurcumin of claim 5, wherein an enhancement of bioavailability of curcumin, dimethoxycurcumin and bisdemethoxycurcumin is observed in a tissue, and wherein the tissue is selected from the group consisting of lungs, heart, kidney, brain, liver, pancreas, stomach, intestine and skin.

* * * * *